United States Patent [19]

Sarnoff

[11] Patent Number: 4,832,682
[45] Date of Patent: May 23, 1989

[54] INJECTION METHOD AND APPARATUS WITH ELECTRICAL BLOOD ABSORBING STIMULATION

[75] Inventor: Stanley J. Sarnoff, Bethesda, Md.

[73] Assignee: Survival Technology, Inc., Bethesda, Md.

[21] Appl. No.: 735,311

[22] Filed: May 20, 1985

Related U.S. Application Data

[63] Continuation-in-part of Ser. No. 460,011, Jan. 21, 1983, abandoned, which is a continuation-in-part of Ser. No. 638,695, Jul. 19, 1984, Pat. No. 4,658,830, which is a continuation-in-part of Ser. No. 708,845, Mar. 6, 1985, Pat. No. 4,661,469.

[51] Int. Cl.$^4$ ............................................. A61M 5/20
[52] U.S. Cl. .................................... 604/21; 604/137; 128/419 R
[58] Field of Search ............ 604/20, 21, 130, 134–137; 128/419–423, 784, 785

[56] References Cited

U.S. PATENT DOCUMENTS

| | | |
|---|---|---|
| 2,771,554 | 11/1956 | Gratzl . |
| 3,078,850 | 2/1963 | Schein et al. . |
| 3,364,929 | 1/1968 | Ide et al. . |
| 3,380,449 | 4/1968 | Sarnoff . |
| 3,391,695 | 7/1968 | Sarnoff . |
| 3,424,155 | 1/1969 | Sarnoff . |
| 3,565,080 | 2/1971 | Ide et al. . |
| 3,807,411 | 4/1974 | Harris et al. . |
| 3,882,863 | 5/1975 | Sarnoff et al. . |
| 4,031,893 | 6/1977 | Kaplan et al. . |
| 4,103,690 | 8/1978 | Harris . |
| 4,226,235 | 10/1980 | Sarnoff et al. . |
| 4,394,863 | 7/1983 | Bartner . |
| 4,658,830 | 4/1987 | Sarnoff .............................. 128/696 |

OTHER PUBLICATIONS

Frans Van de Werf, M.D. et al., *The New England Journal of Medicine*, "Coronary Thrombolysis with Tissue-Type Plasminogen Activator in Patients with Evolving Myocardial Infarction", Mar. 8, 1984, vol. 310, No. 10, pp. 609–613.

Keith A. A. Fox, et al., *Biochemical Pharmacology*, Commentary, "Coronary Thrombolysis: Pharmacological Considerations with Emphasis on Tissue-Type Plasminogen Activator (t-PA)", vol. 33, No. 12, pp. 1831–1838.

Lawrence K. Altman, *The New York Times*, "Protein of Cancer Cells Used to Halt Coronaries", Nov. 16, 1983.

*Primary Examiner*—Stephen C. Pellegrino
*Attorney, Agent, or Firm*—Cushman, Darby & Cushman

[57] ABSTRACT

A method of treating a patient with liquid medicament under circumstances where intravenous injection is not practical but the fast response time of an intravenous injection is desirable, including the treatment of individuals undergoing heart attack symptoms with t-PA. The method comprises the steps of injecting the liquid medicament t-PA preferably with a blood absorption enhancing agent such as hydroxylamine hydrochloride into the muscle tissue of the patient, applying to the patient which has received the injection repeated blood flow stimulating cycles, each of which includes a period of electrical stimulus during which the muscle tissue which has received the injection tenses followed by a period of no electrical stimulus during which the muscle tissue which received the injection is allowed to relax inducing enhanced blood flow within the muscle tissue, and continuing the application of the repeated blood flow stimulating cycles until the injected liquid medicament has been sufficiently absorbed into the enhanced blood flow to achieve a desired possible patient response of reperfusion and apparatus for carrying out the method.

37 Claims, 9 Drawing Sheets

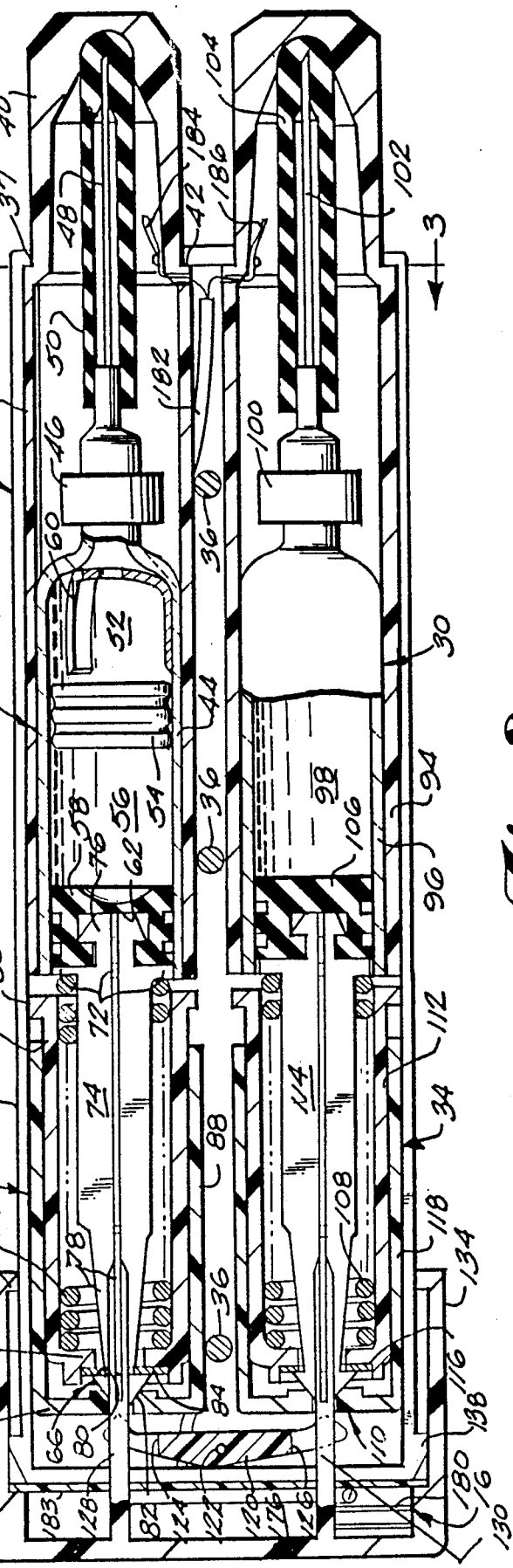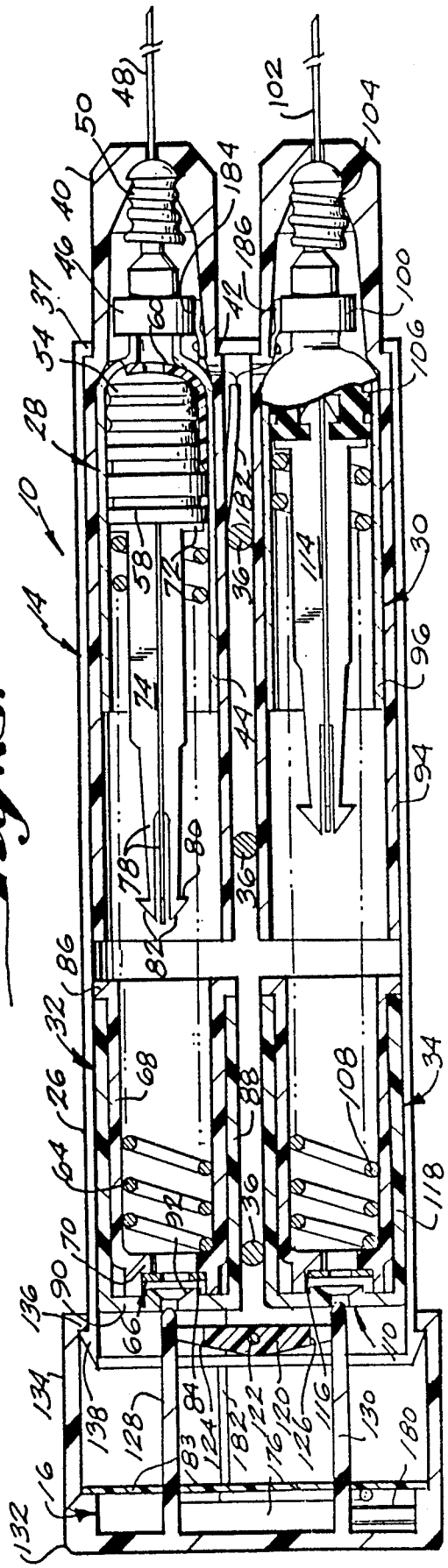

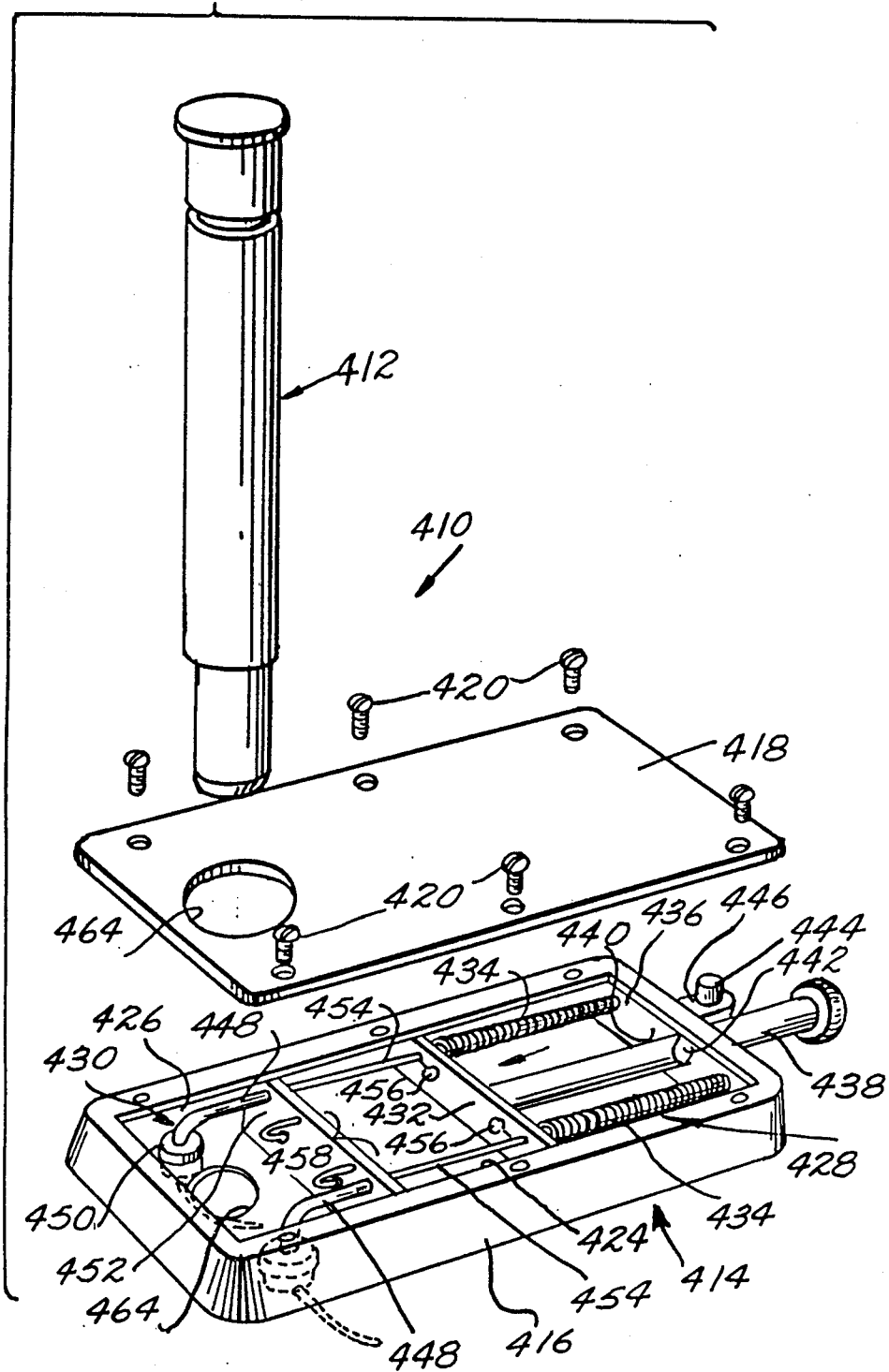

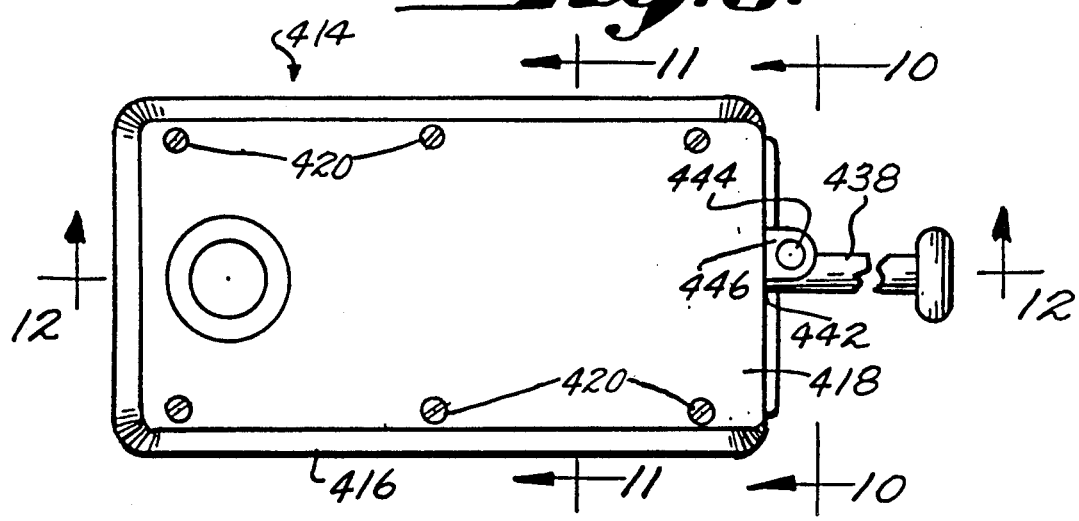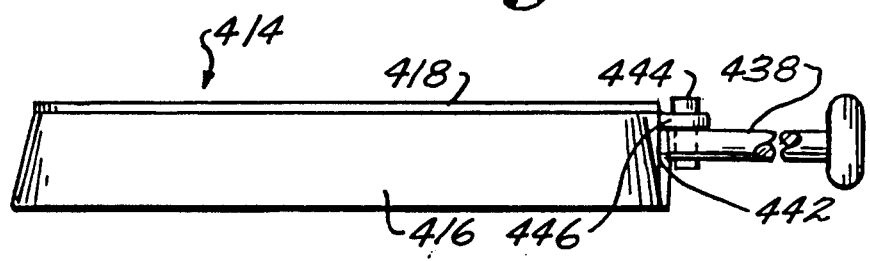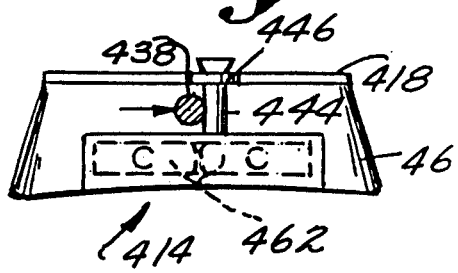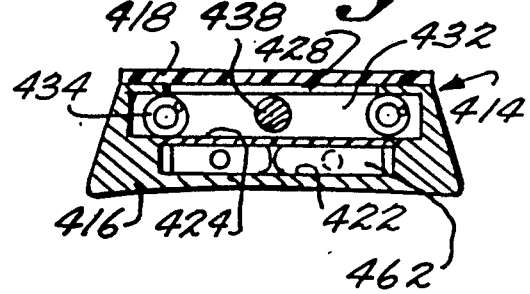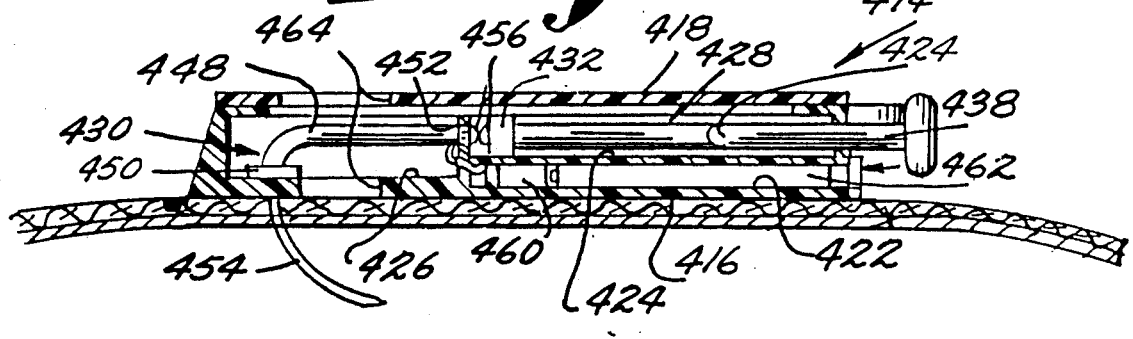

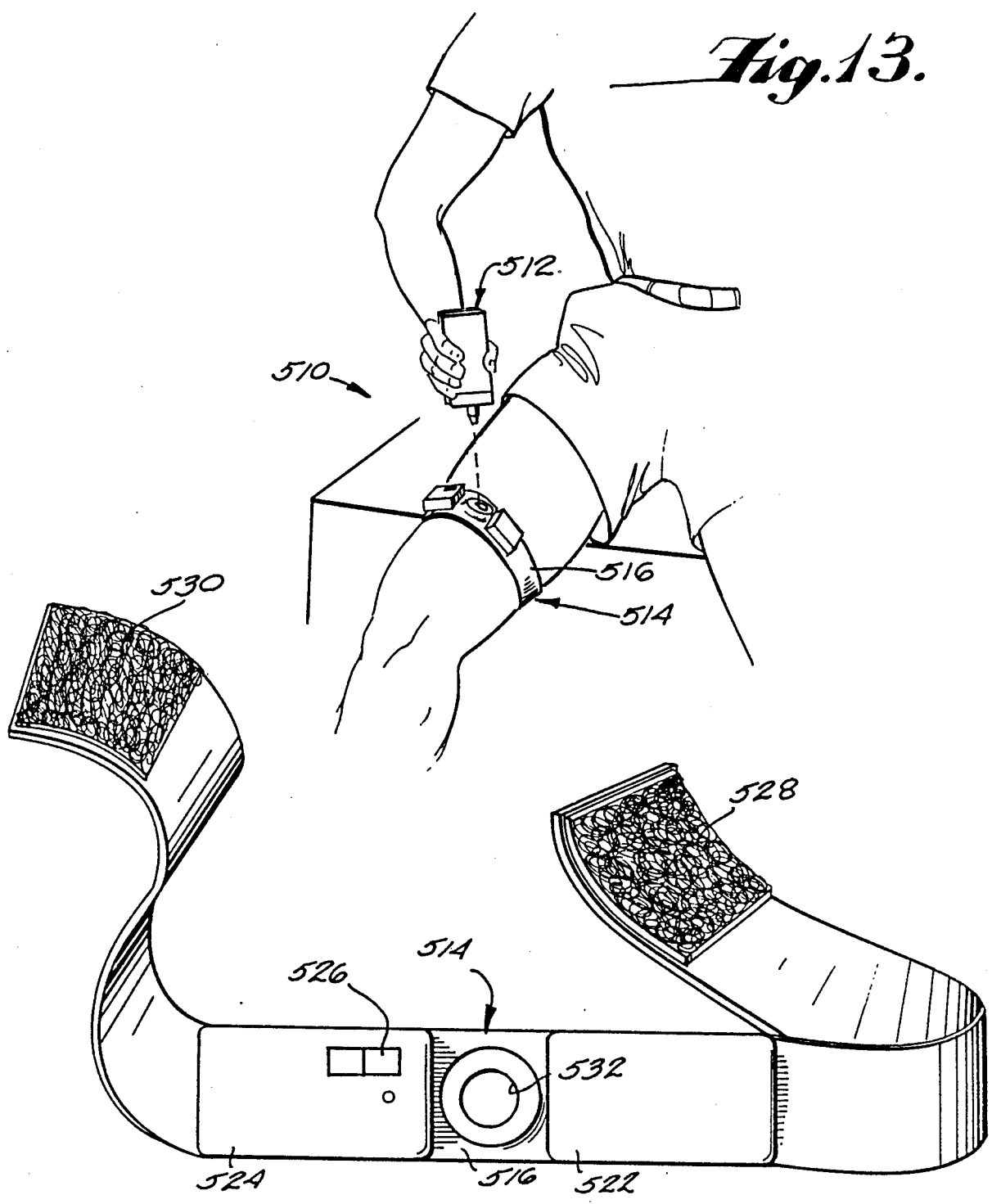

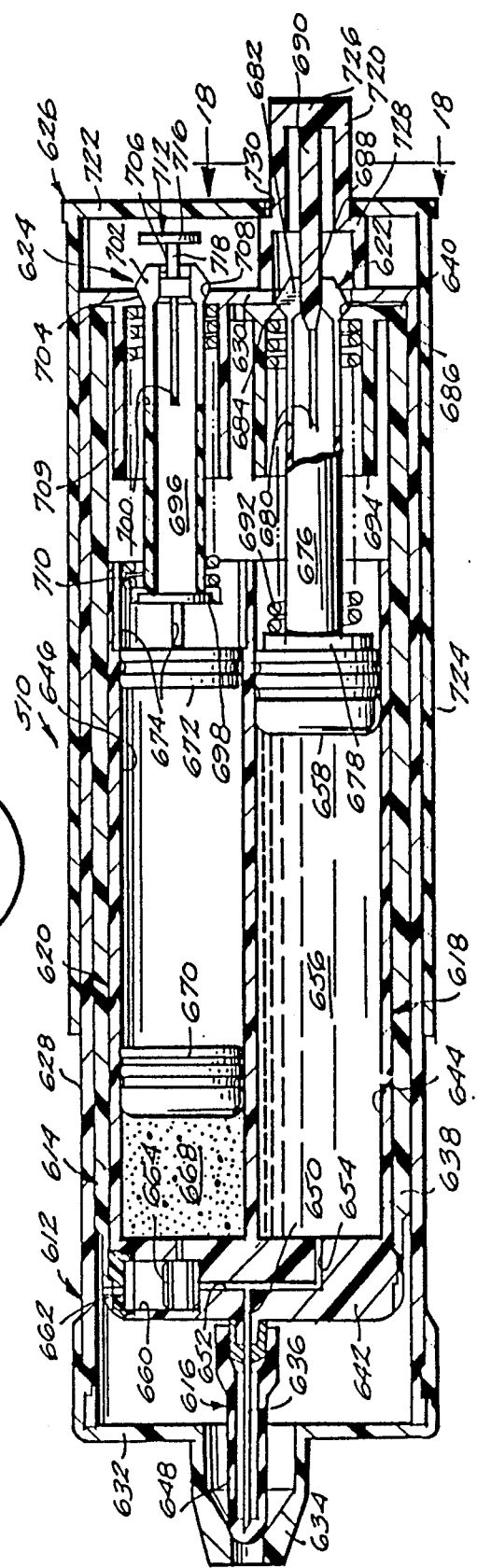

INJECTION METHOD AND APPARATUS WITH ELECTRICAL BLOOD ABSORBING STIMULATION

This application is a continuation-in-part of my copending patent application Ser. No. 460,011 filed Jan. 21, 1983, entitled Injection Method and Apparatus with Electrical Blood Absorbing Stimulation now abandoned, a continuation-in-part of my copending patent application Ser. No. 638,695 filed July 19, 1984 entitled Method and Apparatus for Initiating Reperfusion Treatment by an Unattended Individual Undergoing Heart Attack Symptoms now U.S. Pat. No. 4,658,830, and a continuation-in-part of my copending patent application Ser. No. 708,845 filed Mar. 6, 1985 entitled t-PA Composition Capable of Being Absorbed into the Blood now U.S. Pat. No. 4,661,469.

This invention relates to the treatment of patients by medicament injection and more particularly to medicament injection treatment under circumstances where intravenous injection is not practical but the fast response time of an intravenous injection is desirable.

There are many medical situations presented where it is desirable to treat a patient with a liquid medicament but because of the circumstances which usually are of an emergency nature it is not practical to accomplish intravenous injection but still it is important to achieve the fast response time of an intravenous injection. An intramuscular injection presents a much more practically achievable mode of delivery particularly where the liquid medicament is contained in an automatic injector. An automatic injector is easy to handle safely before use and contains the correct dosage of the medicament to be injected. Injection can be easily accomplished by undertaking a few simple actuating procedures. Moreover, because injection is accomplished by spring pressure, a very favorable distribution of the liquid medicament into the muscle tissue is achieved. Nevertheless, many liquid medicaments once injected into the muscle tissue are not absorbed into the blood stream at rates sufficient to achieve the desired blood concentration level within the time available under the emergency conditions that prevail.

One set of circumstances where these conditions are presented is in the treatment of convulsions induced by soman poisoning under emergency nerve gas warfare situations.

It is well known that soman presents the most difficult nerve gas to deal with from an antidote treatment and personnel rehabilitation point of view. One of the most severe aspects of personnel soman intoxication is the convulsions which are induced. Soman poisoning induced convulsions are often accompanied by lack of breathing, presenting a lethal situation if not rapidly treated.

Known anti-convulsant drugs require intravenous injection in order to provide sufficient rapidity of response to be effective. Intravenous injections are difficult to administer to persons in the throes of convulsions even in hospital situations where more than one person is in attendance. In an emergency situation where a single medic may be required to administer to twenty or more individuals, intravenous injection constitutes a most impractical method of treatment.

Valium is an acceptable anti-convulsant when given intravenously. When injected in the muscle the response time may not be sufficiently rapid to prevent death by suffocation (lack of breathing) of a soman induced convulsive patient. One reason for this slow response time is because valium is not water soluble. Known solvents for valium include propylene glycol which accounts for much of the slow response time. Recently developed Benzodiazepines which are water soluble (e.g. Midazolam) promise increased response times but may suffer from other drawbacks.

Another, perhaps more important, set of circumstances where these conditions are presented is in initiating reperfusion treatment by an unattended individual undergoing heart attack symptoms.

When a clot forms in a blood vessel, the body organ being supplied with blood by that blood vessel is compromised or totally deprived of blood supply. Depending on the blood vessel in which this occurs, the threat to the life of the individual is either small or very great as in the circumstances to be addressed by the material below, i.e. certain life threatening circumstances. Clot formation in a vessel is described as thrombosis. Substances which dissolve thrombi are called thrombolytic substances. When a coronary artery clot is dissolve, the resultant establishment of blood flow to the heart is called reperfusion.

Examples of life threatening clot formation in arterial vessels are cerebral thrombosis, renal thrombosis, opthalmic artery thrombosis, and very importantly, thrombosis of a coronary artery. In approximately 85% to 90% of cases of acute myocardial infarction (coronary heart attack), a thrombus is found in the coronary artery preventing blood from flowing to the heart muscle (myocardium) and supplying it with essential oxygen and other nutrients. A consequence of a thrombus or clot forming in a coronary artery is the danger to the myocardium (heart muscle tissue that does the pumping of blood). Heart muscle deprived of it's blood supply does not die immediately but does begin the process of becoming dead. The extent of the damage which is done to the heart muscle is, therefore, a function of the time during which the supply of blood to the infarct zone is restricted by the clot or occlusion.

Heretofore, the procedures undertaken to actually establish reperfusion to the infarct zone have always been undertaken in a hospital environment or equivalent. The so-called "pre-hospital" treatment was, in general, directed toward keeping the patient alive and getting the patient into the hospital environment as soon as possible so that treatment minimizing the heart muscle damage could be accomplished.

The treatment undertaken in the hospital environment involves certain procedures for establishing reperfusion in the infarct zone of the patient's heart. Where immediate surgery was not clearly indicated, the establishment of reperfusion was accomplished by procedures which had the effect of unblocking the occlusion. The available procedures included mechanical catheterization and the administration of thrombolytic agents. Known thrombolytic agents, such as streptokinase or urokinase required intercoronary infusion or the slow infeed of the agent within the vessel at the site of occlusion by means of a catheter. In recent years, intravenous infusion of streptokinase has been shown to be effective.

More recently a substance called tissue type plasminogen activator or t-PA has been utilized experimentally. (*The New England Journal of Medicine,* Mar. 8, 1984, Vol. 310, No. 10, pp. 609–613). Unlike other plasminogen activators, such as streptokinase or urokinase, t-PA—which is found in only small amounts in the body—acts specifically on clots and not on other proteins in the blood, when maintained at appropriate and effective levels.

A 1984 Commentary found in *Biochemical Pharmacology* Vol. 33, No. 12, pp. 1831–1838 entitled "Coronary Thrombolysis: Pharmacological Considerations with Emphasis on Tissue-Type Plasminogen Activator (t-PA)" contains the following conclusionary statement:

> "Selection of pharmacological agents for induction of coronary thrombolysis has been determined largely by availability. Unfortunately, both streptokinase and urokinase induce a systemic lytic state with depletion of circulating fibrinogen plasminogen, and $_2$-antiplasmin, and accumulation of fibrin degradation products. All of these factors conspire to set the stage for hemorrhage with a risk of serious bleeding. Intravenous administration of these agents is limited by a lower success rate, in part because the upper bound of dose is constrained by the risk of inducing a severe systemic lytic state.
>
> The probability that progress in recombinant DNA technology will lead to widespread availability of tissue-type plasminogen activator is particularly exciting because of the clot specific properties of t-PA. For coronary thrombolysis its potential advantages include: safety and efficacy of intravenous administration of high doses; effective clot lysis without induction of a systemic lytic state; prompt implementation without the need for extensive characterization of the coagulation and fibrinolytic systems in each patient prior to and during therapy; avoidance of frank allergic reactions or variations in dose-response relation due to immune complex formation; ease of minute-by-minute adjustment of dosage and prompt termination of fibrinolysis when needed because of the short biological half-life of t-PA and the lack of induction of a systemic lytic state."

The promise attributable to t-PA administration was discussed at a news conference at a meeting of the American Heart Association and reported by the New York *Times* on Nov. 16, 1983, in an article entitled, "Protein of Cancer Cells Used to Halt Coronaries." The article refers to injection of t-PA by stating the following: "The protein [t-PA] can simply be injected into the vein in the arm of the patient seized by a myocardial infarction or heart attack, and it travels through the blood to dissolve a clot, in much the same way as Draino clears up stopped plumbing."The article further indicated under the subheading "Hopes for Future Application" that many physicians have expressed excitement about research into the use of t-PA to treat heart attacks because they hope that some day it may be used in emergency rooms and ambulances to stop heart attacks at their earliest stages before they kill or cause permanent damage. Under the "Hopes for Future Application" subheading there is also included the following paragraph: "Dr. Burton E. Sobel of Washington University, one of the researchers, speculated that patients might some day carry a vial with them so that the drug could be injected immediately after they felt chest pain and other early symptoms of a heart attack."

In medical parlance, a vial is a container for a quantity of liquid medicine or diluent having a rubber stopper capable of being pierced by a hypodermic needle of a syringe to enable the operator of the syringe to withdraw a predetermined dosage of the liquid from the vial. In the case of t-PA, the dosage could the be injected into the mother liquid container of an infusion assembly. The necessity to administer the drug by slow intravenous infusion or by slow intravenous injection presents a significant barrier to self-administration from a practical view point, particularly when considering the disconcerting circumstances of the individual undergoing the symptoms of a myocardial infarction.

The development of an effective self-administration procedure for t-PA sufficient to enable its utilization by a targeted coronary prone individual immediately following onset of symptoms, would materially increase the potential efficacy of t-PA as a thrombolytic agent by insuring its use at the earliest possible time often before irreversible heart muscle damage has occurred, and, at the same time, provide a treatment of the pre-hospital or pre-ambulance type which for the first time is directly effective to minimize heart muscle damage accompanying myocardial infarction.

With respect to t-PA, a severe threshold question is presented as to whether an intravenous injection would be effective. Even though t-PA may be regarded as a clot selective thrombolytic agent, when introduced into the blood stream at a predetermined level, tests thus far performed show that the concentration can be increased to the point that a systemic lytic state can be induced. Intramuscular injection involves the introduction of a concentrated dosage of t-PA in an area contiguous to and substantially surrounding the wound caused by the penetration and withdrawal of the injection of the hypodermic needle. Consequently, it would be expected that at least a localized lytic state would be induced resulting in hemorrhage from the needle wound. Unexpectedly, tests have shown that no such hemorrhage does in fact occur.

Beyond this threshold question, exists the question of whether sufficient quantities of the t-PA injected into the muscle tissue would be absorbed in time to be effective. t-PA is a large protein. It would not be expected that it would be absorbed into the blood stream in discernible quantities. Extra-vascular levels of protein are about 1/10 that of intravascular protein. It is thought that this is so because the capillary pores through which transport of protein can occur are small relative to the molecular size of protein and limit protein transport because of electrical charge. It was thus highly problematical as to whether a large protein such as t-PA, when given intramuscularly, i.e. outside the blood vessels, would find its way rapidly into the blood stream in discernible quantities. Applicant tests have shown that unexpectedly t-PA does find its way rapidly into the blood stream in discernible quantities after intramuscular injection.

In accordance with the principles of the present invention, enhancement of blood absorption of t-PA is accomplished in two ways. First, by injecting a blood absorption enhancing agent, such as hydroxylamine hydrochloride, into the muscle tissue along with the t-PA and second, by applying blood absorption enhancing electrical stimulating cycles. Moreover, in order to provide for total treatment it is within the contemplation of the present invention to also inject into the muscle tissue with the t-PA an anti-arrhythmic agent, such as lidocaine, an anti-reclotting agent, which may be either a thromboxane synthetase inhibitor, such as dazoxiben, or an antagonist for the receptor of thromboxane A, such as SQ 27,427 and a reperfusion damage preventing agent, such as superoxide dismutase (SOD) or S-aminotrimethyleneaminoethyl thiophosphate.

In so far as the invention has applicability beyond the use with t-PA, it is a further object of the present invention to provide a method and apparatus which will enhance the blood absorption of any intramuscularly injected medicament under circumstances of the type noted above where intravenous injection is not practical but the fast response time of an intravenous injection is desirable.

In accordance with the principles of the present invention this objective is accomplished by injecting a dosage of the liquid medicament into the muscle tissue of the patient and applying to the patient who has received the injection repeated blood flow stimulating cycles, each of which includes a period of electrical stimulus during which the muscle tissue which received the liquid medicament tenses followed by a period of no electrical stimulus during which the muscle tissue which received the liquid medicament is allowed to relax inducing enhanced blood flow within the muscle tissue and continuing the application of the repeated blood flow stimulating cycles until the injected medicament has been sufficiently absorbed into the blood to achieve patient response.

A further object of the present invention is the provision of apparatus for effecting the aforesaid treatment method. Preferably, the injecting means of the apparatus constitutes an automatic injector of the type including a stressed spring releasable by a releasing mechanism actuated in response to the accomplishment of a predetermined muscle actuating procedure. Preferably, the electrical blood flow enhancing cycle applying means includes a pair of electrode elements capable of being operatively applied to the patient through which an electrical circuit is completed so as to directly stimulate the muscle tissue receiving the injection or to stimulate the nerves controlling the muscle tissue receiving the injection so that the aforesaid blood flow stimulating cycles can be repeated.

Another object of the present invention is the provision of an apparatus of the type described which is simple in construction, effective in operation and economical to manufacture.

These and other objects of the present invention will become more apparent during the course of the following detailed description and appended claims.

The invention may best be understood with reference to the accompanying drawings wherein illustrative embodiments are shown.

In the drawings:

FIG. 1 is a sectional view of one form of an apparatus embodying the principles of the present invention showing the position of the parts in their storage position;

FIG. 2 is a view similar to FIG. 1 showing the position of the parts after the medicament dosage has been injected and the electric blood flow stimulating circuit is still in operation;

FIG. 7 is a partially exploded perspective view of still another apparatus embodying the principles of the present invention;

FIG. 8 is a plan view of the blood flow stimulating device of the apparatus shown in FIG. 7;

FIG. 9 is a side elevational view of the device shown in FIG. 8;

FIG. 10 is a sectional view taken along the line 10—10 of FIG. 9;

FIG. 11 is a sectional view taken along the line 11—11 of FIG. 8;

FIG. 12 is a sectional view taken along the line 12—12 of FIG. 8;

FIG. 13 is a pictorial view illustrating still another apparatus embodying the principles of the present invention showing the same in use by a FIG. 14 is a top plan view of the blood flow enhancing cycle applying assembly shown in FIG. 13;

FIG. 17 is a sectional view of the automatic injector shown in FIG. 13; and

FIG. 18 is a sectional view taken along the line 18—18 of FIG. 17.

Figure 3:
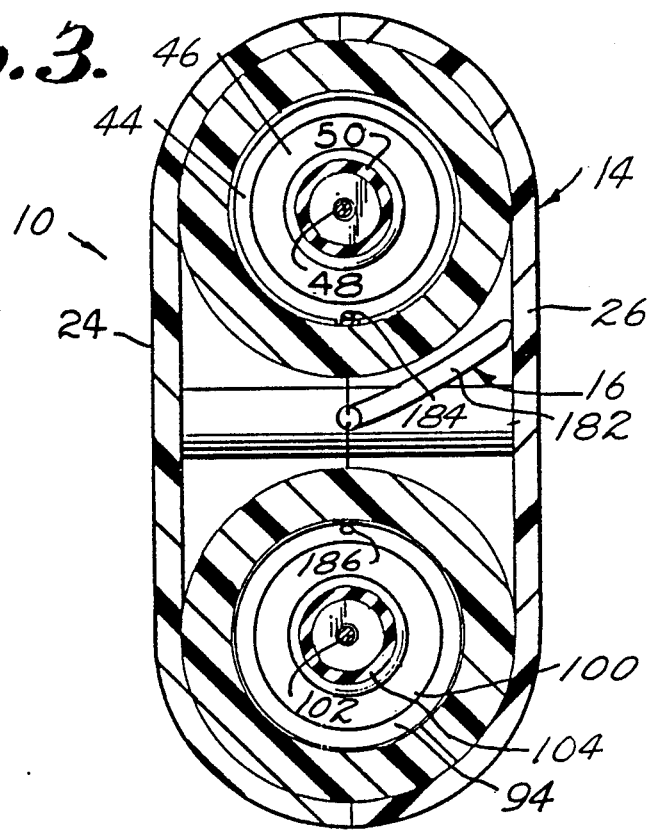
FIG. 3 is an enlarged sectional view taken along the line 3—3 of FIG. 2.

Referring now more particularly to FIGS. 1-4 of the drawings, there is shown therein one form of an apparatus embodying the principles of the present invention which is generally indicated by the numeral 10. The apparatus 10 includes an automatic injector assembly, generally indicated at 14, and an electric blood flow stimulating assembly or device generally indicated at 16. The automatic injector assembly 14 is preferably constructed in accordance with U.S. Pat. No. 4,226,235 modified to provide electrical circuitry which cooperates with the electrical blood flow stimulating assembly 16 in a manner hereinafter to be more fully described.

As shown, the automatic injector assembly 14 includes an outer housing in the form of two separate outer housing halves 24 and 26 molded of a suitable moldable material, such as plastic. The housing halves, when disposed together, provide chambers suitable to receive therein first and second medicament cartridge assemblies 28 and 30 and respective first and second power pack units or stressed spring assemblies 32 add 34. The two housing halves 24 and 26 are arranged to be rigidly secured together in operative relation with respect to the assemblies 28, 30, 32 and 34 by a plurality of spacer rivets 36 which serve not only to rigidly secure the two housing halves together inoperative relation but to retain the first cartridge and stressed spring assemblies in cooperating relation and the second cartridge and stressed spring assemblies within the outer housing in side by side spaced relation. As shown, the housing halves 24 and 26 are provided with mating flanges 37 at their forward ends.

Mounted within a first one of the chambers provided by the housing halves 24 and 26 is a first container support 38 in the form of a tubular member having the major portion thereof formed with a cylindrical exterior periphery slidably fitting within the forward end portion of the chamber provided by the housing halves 24 and 26. The tubular member 38 includes a forwardly outwardly extending nose portion 40 of an exterior cylindrical configuration sufficient to extend through an opening in the flanges 37. The exterior transition between the nose portion 40 and the remainder of the tubular member 38 provided an annular shoulder 42 which is adapted to normally engage the associated adjacent portions of the flanges 37.

Slidably mounted within the tubular member 38 is a first glass or plastic ampule or liquid medicament container 44. Preferably, the container is formed of glass, generally in the form of a necked bottomless bottle. Fixed to the necked end of the container 46 is a hub assembly 46 carrying a longitudinally forwardly extending hypodermic needle 48. The exterior of the hypodermic needle 48 is covered by a shock absorbing resilient sheath 50 in accordance with the teachings contained in commonly assigned Sarnoff et al. U.S. Pat. No. 3,882,863. The hub assembly 46 provides an interior resilient diaphragm (not shown) constructed in accordance with the teachings contained in commonly assigned Sarnoff et al. U.S. Pat. No. 3,391,695. The diaphragm serves to seal the metallic material which forms the hypodermic needle 88 from the interior of the container 44 which has in the forward end portion thereof a liquid medicament, indicated by the numeral 52, containing a clot selective coronary thrombolytic agent, such as, for example t-PA.

The t-PA medicament 52 is sealingly retained in the container by a movable stopper 54 which, as shown, is in the form of a piston of resilient material. The preferred exemplary amount of the liquid medicament 52 is an amount of t-PA sufficient to be absorbed into the blood from an appropriate ultramuscular injection site to establish a t-PA blood plasma level of from 5 to 750 International (urokinase equivalent) units per milliliter of blood plasma. Based upon the animal studies thus far undertaken, it would appear that an intramuscular dosage of 1 milligram of t-PA per kilogram of body weight is one example of a dosage which would be suitable to produce a t-PA plasma level of from 5 to 750 International (urokinase equivalent) units per milliliter of blood plasma.

As shown, the medicament 52 is of a volume somewhat less than the total capacity of the container 44 and a second liquid medicament, indicated at 56, is mounted within the container rearwardly of the stopper 54. Liquid medicament 56 contains a blood absorption enhancing agent, such as, for example, hydroxylamine hydrochloride. An example of the amount of hydroxylamine hydrochloride which is included in the liquid medicament 56 is an mount of 2 to 85 milligrams per kilogram of body weight. The liquid medicament 56 is sealingly contained in the container 44 by a piston 58 of resilient material. The piston 58 thus forms a part of the plunger means which serves to move both liquid medicaments 52 and 56 outwardly through the hypodermic needle 48 after the diaphragm has been ruptured through hydraulic pressure. A by-pass fitment 60 is mounted in the forward end of the container 44 for insuring that the rearward medicament 56 will be moved around the stopper 54 after the first medicament has been discharged from the container 44. Fitment 60 is constructed in accordance with the teachings contained in commonly assigned U.S. application Ser. No. (735,740) filed concurrently herewith. Other by-pass arrangements may be utilized such as disclosed in commonly assigned U.S. Pat. No. 4,394,863.

The stressed spring assembly 32 includes a first coil spring 64 retained in stressed condition by a first releasing mechanism, generally indicated at 66. The releasing mechanism 66 includes an inner tube or sleeve 68 having an interior cylindrical periphery of a size sufficient to receive the spring 64 therein. At the rearward end of the sleeve 68 is a radially inwardly extending flange 70 which serves to abuttingly receive the rearward end of the stressed spring 64. The forward end of the stressed spring 64 extends outwardly from the opposite end of the inner tube or sleeve 68 and is engaged by a plurality of outwardly extending tabs 72 formed on the forward end portion of an elongated collet member 74 made up of two interfitted stampings. The forward end of the collet member 74 adjacent the tabs 72 is formed with tongues 76 of a size to engage within the socket 62 in the end of spacer 58. The collet member 74 extends rearwardly from the tabs 72 through the interior of the spring 64 and has formed on the opposite rearward end thereof spring fingers 78 having forwardly facing locking shoulders 80 formed on the exterior thereof and rearwardly and inwardly inclined cam releasing surfaces 82 on the exterior rearward extremities thereof. The locking shoulders 80 are adapted to engage a suitable locking disk 84 engaged with the rearward surface of the flange 70 of the inner tube 68.

The forward end of the inner tube 68 is formed with a radially outwardly extending annular flange 86 which is spaced from the forward end of an outer tube 88 forming a part of the releasing mechanism 66. The outer tube 88 is slidably mounted over the exterior periphery of the inner tube 68 and has at its rearward end a centrally apertured end wall 90 having a forwardly and outwardly inclined frustoconical cam surface 92 formed on the central portion thereof disposed in engagement with the inclined cam surfaces 82 on the spring fingers 78. The container support member 38, container 44, liquid medicaments 52 and 56, hub 46, needle 48, sheath 50, stopper 54 and piston 58 constitute the first cartridge assembly 28 and the spring 64, inner tube 68, collet member 74, outer tube 88 and locking disk 84 constitute the first stressed spring assembly 32 for operating the first cartridge assembly 28.

The second cartridge assembly 30 is similar to the first and includes a second container support member 94, a second container 96, a third liquid medicament 98, a second hub 100, a second needle 102, a second sheath 104, and a second piston 106. The second stressed spring assembly 34 is similar to the first and includes a second spring 108, a second releasing mechanism 110, a second inner tube 112, a second collet member 114, a second locking disk 116 and a second outer tube 118.

In accordance with the principles of the present invention, the third medicament 98 contains a cardiac anti-arrhythmic agent, as, for example, lidocaine. An exemplary intramuscular dosage of lidocaine for present coronary anti-arrhythmic purposes is 300 milligrams contained in 3 milliliters of liquid.

It will be noted that the housing halves 24 and 26 are extended rearwardly to receive therein a lever 120. Lever 120 has its central portion pivoted to the extended rearward end of the housing halves 24 and 26 by a pivot pin 122 suitably mounted between the housing halves 24 and 26. The outer ends of the lever 120 are bifuracted, as indicated at 124 and 126, so as to receive therebetween safety pins 128 and 130 respectively forming a part of separate safety cap 132. Cap 132 is normally disposed in a release preventing position at the rear end of the housing halves 24 and 26. In this position pin 128 extends through the centrally apertured end wall 90 into position within the spring fingers 78 of the collet member 74 thus preventing radially inward deflecting of the spring fingers. Safety pin 130 extends forwardly into a similar position with respect to the second outer tube 118 and the second collet member 114.

The safety cap 132 also includes an outer skirt element 134 which is shaped to engage over the rearward end portion of housing halves 24 and 26 forming the outer housing. As shown, when the safety pins 128 and 130 are in the normal storage position, as shown in FIG. 1, the inner edge of the skirt element 134 is spaced inwardly from the rearward end of the housing. The inner periphery of the skirt element 134 is spaced outwardly from the adjacent exterior periphery of the outer housing and its inner extremity is formed with an inwardly directed tapered abutment or annular shoulder 136. The housing halves 24 and 26 are formed with similar outwardly extending abutment shoulders 138. It will be noted that when the safety cap 132 is moved rearwardly with respect to the outer housing, the safety pins 128 and 130 will be removed from between the associated spring fingers 78 and 114 enabling the stressed spring assemblies 32 and 34 to be actuated. The interengagement of the abutment shoulders 136 and 138 serves to retain the safety cap 132 with the outer housing when the former is in a position to permit actuation.

The electric blood flow stimulating assembly 16 of the present invention is operable to apply to the muscle tissue which has received the injection repeated blood flow stimulating cycles, each of which includes a period of electrical stimulus of the muscle tissue during which the muscle tissue tenses followed by a period of no electrical stimulus during which the muscle tissue is allowed to relax, inducing enhanced blood flow within the muscle tissue. Moreover, the repeated blood flow stimulating cycles are continued until the injected medicament has been sufficiently absorbed into the blood to achieve a desired patient response where possible.

The electrical stimulus is provided by a conventional dry cell battery 176 which for the sake of convenience is mounted within the rear end portion of the safety cap 132. The battery 176 is connected to an electric circuit 180 which serves to convert the DC electrical current coming from the battery to the repeated blood flow stimulating cycles as aforesaid. The circuit 180 is connected to the needles 48 and 102 when the latter are extended into penetrating relation with the muscle tissue of the patient so as to complete an electric circuit through the tissue between the needles during the period of electrical stimulus of each cycle. To this end, there is provided a two-lead wire 182 which extends from the circuit 180 through a cover plate 183 within the safety cap 132, then through the rear end of the housing half 26 and then longitudinally forwardly through the latter in a loosened or slack fashion to a position adjacent the forward end portion thereof. As shown, one lead of the wire 182 extends to a contact 184 which is disposed within the adjacent interior periphery of the tubular support member 38. The other lead of the wire 182 is extended to a contact 186 disposed on the interior periphery of the tubular member 94. It will be understood that the contacts 184 and 186 are engaged by tee exterior periphery of the hubs 46 and 100 when the needles 48 and 102 are in muscle penetrating relation with the patient.

Figure 4:
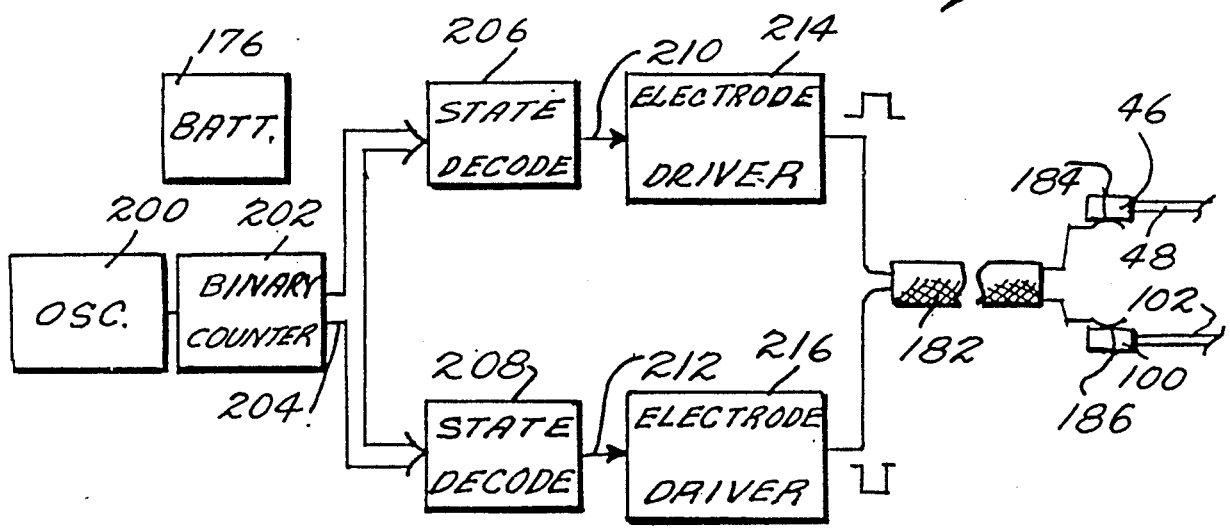
FIG. 4 is a schematic electrical diagram showing the electric blood flow stimulating circuit of the apparatus shown in FIGS. 1-3.

FIG. 4 discloses an exemplary embodiment of an electrical circuit 180 for converting the continuous DC current source provided by the battery 176 into the repetitive blood stimulating cycles. In this regard it will be noted that the cycle frequency may be varied and that the ratio of the period of electrical stimulus with respect to the period of no electrical stimulus in each cycle may likewise be varied. Moreover, while it is within the contemplation of the present invention to provide the electrical stimulus by the circuit in such a way that the flow of current is always from one of the needles to the other, it is preferable to alternate the direction of current flow so that every other period of electrical stimulus is in one direction while the alternative periods are in the opposite direction. An example of the range of variation of the frequency of the cycles is from one cycle every two seconds to 30 cycles per second. The ratio of the electrical stimulus periods with respect to the no electrical stimulus periods varies depending upon the cycle frequency.

In general the ratio between the electrical stimulus period to the period of no electrical stimulus should be relatively low, that is, the period of electrical stimulus should be relatively short with respect to the period of no electrical stimulus. A preferred embodiment is to provide four cycles per second with the period of electrical stimulus being 245 milliseconds. It is important to provide a period of no electrical stimulus which is sufficient to allow the muscle tissue to relax so as to induce enhanced blood flow within the muscle tissue. Where the frequency is sufficiently great as, for example, of the order of forty cycles per second and greater, or the period of no electrical stimulus is relatively short, the resultant muscular effect is one of substantially continuous tenseness, thus inhibiting rather than inducing blood flow.

Referring now to FIG. 4, there is shown a block diagram of the presently preferred configuration of circuit 180. Dry cell battery 176 is constituted by a battery pack supplying from 3 v to 18 v for powering operating circuit 180 for generating those cycles. The heart of circuit 180 is an oscillator 200 providing 1024 pulses per second. This frequency is preferred for establishing four cycles per second. Of course, other oscillator frequencies could be utilized if different timing is desired for the cycles. The output of oscillator 200 is coupled to an 8-bit battery counter 202 for counting the pulses provided by oscillator 200. Binary counter 202 has a multi-bit bus 204 output for providing a multi-bit logic encoded signal indicating the current count of pulses from oscillator 200, resetting occurring automatically after the maximum count is reached. Multi-bit bus 204 is coupled to a first state decoder 206 and to a second state decoder 208. In effect, the state decoders 206 and 208 interpret logic signals on bus 204 to provide output pulses at their respective outputs 210 and 212 at appropriate times. These output pulses are used to trigger the generation of the cycles by electrode drivers 214 and 216. Output 210 of decoder 206 is coupled to the electrode driver 214 for generating a cycle with a first electrical polarity each time a trigger pulse is applied thereto by state decoder 206. Similarly, electrode drive 216 is coupled to output 212 of decoder 208 for generating a second polarity cycle each time a trigger pulse from decoder 208 is applied thereto. Electrode drivers 214 and 216 establish current pulses between needles 48 and 102 through contacts 186 and 184 respectively. In effect, electrode drivers 214 and 216 provide pulses of opposite polarity to one another so as to alternately provide current from needle 48 to needle 102 and from needle 102 to needle 48. The provision of parallel needles in the apparatus 10 between which the electrical stimulated impulses travel is desirable from the standpoint of the amount of muscle tissue surrounding the position of injection which is electrically stimulated.

The apparatus 10 as described above may be used in the system disclosed in my earlier copending application, Ser. No. 708,845 or in any situation where a reperfusion treatment is required under circumstances where an intravenous injection is not practical but the fast response time of an intravenous injection is desirable. The operator of the apparatus 10 operates the injector assembly 14 to effect the injection by undertaking a predetermined actuating procedure which includes removal of the safety cap 132 out of its normal storage position into its rearward actuating position. The remainder of the actuating procedure includes grasping the exterior of the housing halves 24 and 26 and moving the assembly 14 with the cap 132 moved so as to engage the forward end of the tubular members 38 and 94 with the portion of the exposed thigh muscle. Continued forward movement of the housing halves 24 and 26 with respect to the thigh engaged members 38 and 94 results in the release of the releasing mechanisms 66 and 110. The lever 120 insures that both releasing mechanisms will be actuated irrespective of which of the two are initially released by the aforesaid actuating procedure. That is, if the actuating procedure by the individual is such that the members 38 and 94 are engaged simultaneously, then the respective releasing mechanisms will be simultaneously released. The operation of the lever 120 is such that if during the aforesaid movement, the members 38 and 94 are sequentially engaged with the thigh (in either order) sequential release of the associated releasing mechanisms (in a corresponding order) will occur. To illustrate this sequential operation, it is assumed that in moving the assembly 14 into engagement with the thigh muscle, the member 38 is first engaged and then sequentially the member 94.

The actuation of the releasing mechanism 66 occurs immediately following the engagement of the forward portion 40 of the member 38 with the patient's thigh. Continued forward movement on the housing halves 24 and 26 results in the forward movement of the cam engaging surface 92 with respect to the cam surfaces 82 of the spring fingers 78. This movement causes the spring fingers to flex inwardly thus moving locking surfaces 80 out of locking engagement with the locking ring 84. Spring 64 is thus released which results in two movements. One is a rearward movement of the inner tube 68 which engages the associated outer tube 88 and moves the latter rearwardly. The rearward movement of the outer tube rear wall 90 has the effect of applying a rearward force to the bifurcated end 124 of the lever 120 thus causing the bifurcated end 126 to move forwardly. This forward movement causes the releasing mechanism 110 to be released in a manner similar to the releasing mechanism 66.

The initial release of spring 64 also creates a main forward force which is applied to the collet member 74 through the lugs 72. This forward force is transmitted by virtue of the piston 58, liquid medicament 56, stopper 54 and liquid medicament 52 to move the latter together with the container 44, hub 46 and needle 48 forwardly. The forward movement of the needle causes the forward sharpened end thereof to pierce through the resilient sheath 50 and penetrate into the muscle tissue of the thigh of the patient. The forward movement of the needle 48 and the other components moved forwardly therewith is resisted and stopped by compression of the resilient sheath 50. The continued application of the spring force thereafter creates a sufficiently greater pressure within the liquid medicament 52 to cause the diaphragm within the hub 46 to burst. The liquid medicaments 52 and 56 are then sequentially expelled by the continued forward movement of the piston 58 under the applied spring force so as to pass beyond the ruptured diaphragm through the hypodermic needle 48 and outwardly into the muscle tissue of the thigh of the patient. The cartridge assembly 30 functions similarly with respect to liquid medicament under the force applied by the released spring 108 when the releasing mechanism 110 is released as aforesaid.

It can thus be seen that the liquid medicaments 52 and 56 are easily and conveniently injected into the muscle tissue of the thigh of the patient in response to a single predetermined actuating procedure which includes removal of the safety cap 132 from its storage position. Moreover, as soon as the needles 48 and 102 are extended, the electrical blood flow stimulating assembly 16 is operable to apply repeated blood flow stimulating cycles to the patient. The application of the cycles is continued until sufficient medicament is absorbed into the blood to achieve reperfusion.

Figure 5:
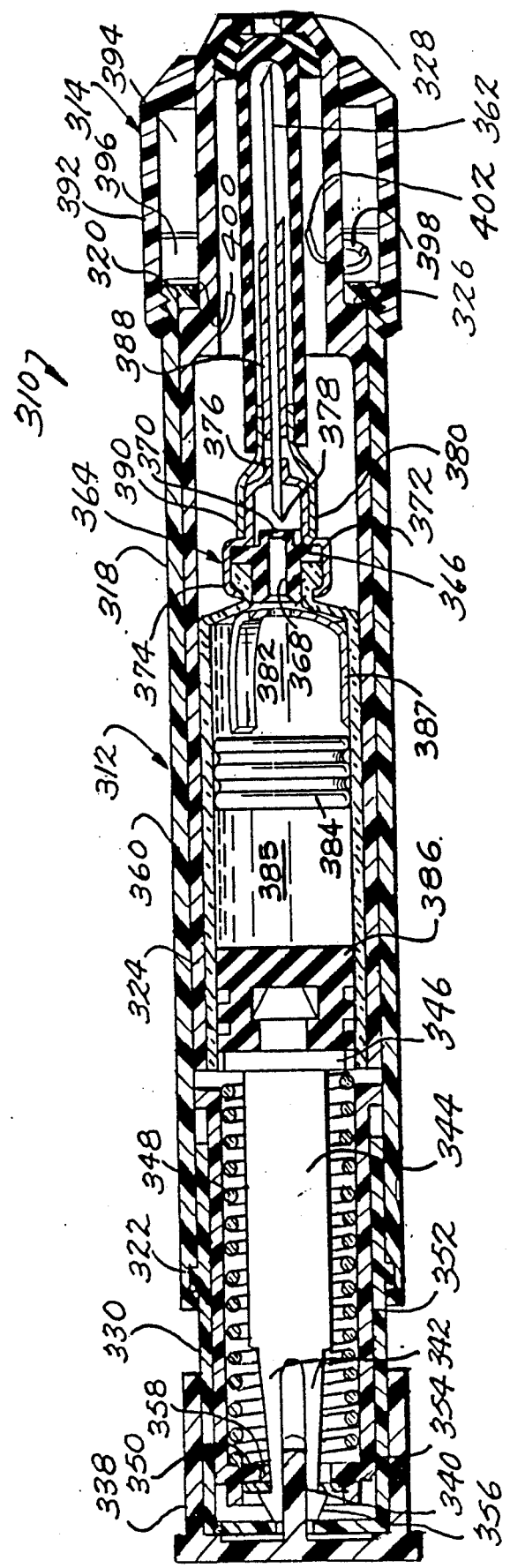
FIG. 5 is a sectional view of another form of apparatus embodying the principles of the present invention showing the parts in a storage position prior to usage.
Figure 6:
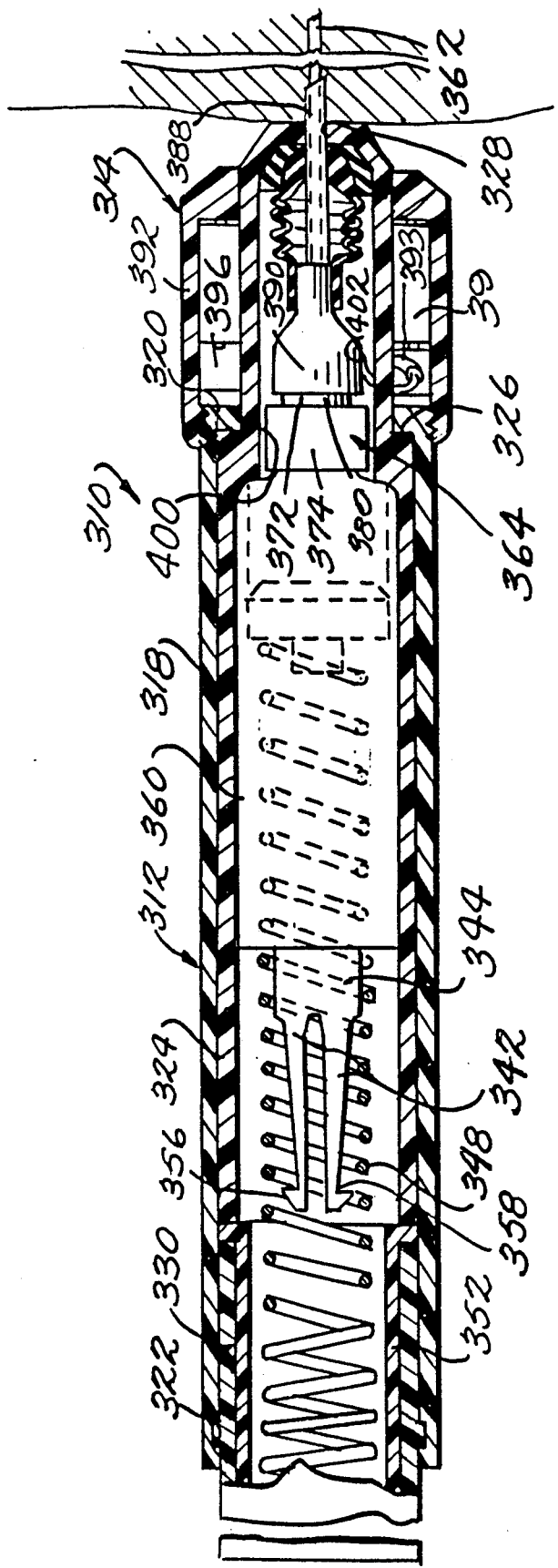
FIG. 6 is a side elevational view partly in section of the apparatus of FIG. 5 showing the position of the parts after the medicament dosage has been injected and the electric blood flow stimulating circuit is in operation.

In FIGS. 5 and 6 there is shown another form of apparatus 310 which embodies the principles of the present invention. The apparatus 310 includes an automatic injecting device 312 which is constructed in accordance with the aforesaid U.S. Pat. No. 4,031,893 and an electric blood flow stimulating device 314 which is incorporated within the forward nd of the device 312.

As best shown in FIG. 5, the automatic injector 12 includes an outer tubular member 318 having a radially inwardly turned flange 320 on the forward end thereof and an interior annular groove 322 in the rearward end thereof. The housing assembly of the device 312 also includes an inner tubular member 324 having a forward end portion of reduced diameter defining an exterior forwardly facing shoulder 326 which is adapted to engage the forward flange 320 of the outer tubular member 318 when the inner tubular member is disposed therein in operative position. The inner tubular member 324 includes a forward end having a needle opening 328 therein and the interior of the inner tubular member is configured to receive the cartridge assembly of the device 312.

The stressed spring assembly of the device 312 as preassembled includes an outer tubular member 330 having an annular ridge 332 formed on the exterior periphery thereof adjacent the rearward end portion which serves to engage within the annular groove 322 of the outer tubular member 318 when the injector is assembled in operative position, as shown in FIG. 5. The outer tubular member 300 includes a rearward end wall 334 having a central opening therein defined by a frustoconical surface 336 which diverges inwardly. The stressed spring assembly includes a safety cap 338 which detachably fits over the portion of the outer member 330 extending rearwardly from the outer tubular member 318. The safety cap 338 includes a central inwardly extending safety pin 340 which in its normal preassembly position extends through and inwardly of the frustoconical surface 336.

The safety pin 340 is adapted to cooperate with a plurality of spring fingers 342 extending from the rear end of a plunger 344 having an annular flange 346 extending rearwardly outwardly from the forward end thereof. The rearward surface of the flange 346 is adapted to engage one end of a stressed coil spring 348, the other end of which engages an apertured rear wall 350 of a tubular member 352 slidably mounted within the tubular member 330. The apertured end wall 350 has formed therein an apertured catch plate or disc 354. The central opening of the catch plate 354 is of a size to engage inclined surfaces 356 formed on the outer rearward portions of the spring fingers 342 so as to deflect the fingers radially inwardly as the rearward ends of the fingers pass rearwardly therethrough. Each spring finger 342 has formed therein an exterior catch receiving notch 358 which is adapted to receive the catch plate 354 when the spring fingers have been moved rearwardly through the catch plate into the normal spring stressed preassembly position, as shown in FIG. 5. In this regard it will be noted that safety pin 340 engages within the inner surfaces of the spring fingers 342 and hence prevents their radially inward movement so that the tubular members 330 and 352, plunger 344 and safety cap 338 can be preassembled and mounted in operative position within the outer tubular member 318 as a unit. In the operative position, the members 330 and 352 of the power pack assembly of the device 312 may be regarded as part of the housing assembly thereof.

The cartridge assembly of the device 312 includes a medicament container 360 which, as shown, is preferably made of glass and is essentially in the form of a necked bottomless bottle having a substantially cylindrical peripheral wall. The cartridge assembly also includes a hypodermic needle 362 which is disposed forwardly of the container 360 and has its rearward end connected with the necked end of the container 360 by a connecting assembly, generally indicated at 364. The connecting assembly 364 is preferably constructed in accordance with the teachings contained in commonly assigned U.S. Pat. No. 3,380,449 (see also U.S. Pat. Nos. 3,391,695 and 3,424,155), the disclosures of all of which are hereby incorporated by reference into the present specification. As shown, the assembly 364 includes a resilient stopper 366 engaged within the necked end of the container 360, the stopper providing a central passage 368 which leads to an exterior integral resilient diaphragm seal 370. Disposed in exterior engagement with the stopper 366 is a ferrule member 372. A rearward sleeve portion 374 of the ferrule member 372 is engaged over the forward marginal and outer periphery of the stopper 366 and the neck portion of the container 360 and has its rearward end turned down to effectively secure the components of the assembly in operative position. A reduced forward end portion 376 of the ferrule member 372 fixedly receives a portion of the hypodermic needle 362 spaced slightly from the rearward end thereof. As shown, the rearward end of the hypodermic needle is sharpened, as indicated at 378, and positioned in forwardly spaced relation from the seal 370 and sealingly surrounded by an intermediate portion 380 of the ferrule member.

The cartridge assembly also includes a forward liquid medicament (t-PA) 382 within the container 360 which is sealed at its forward end by diaphragm seal 370 and at its rear by a resilient stopper 384. As before, a rearward liquid medicament hydroxylamine hydrochloride 385 is disposed within the container 360 rearwardly of the stopper 384. The medicament 385 is sealed rearwardly by a resilient piston 386. Also, as before a by-pass fitment 387 is mounted in the forward end of the container 360.

The electric blood flow stimulating device 314 consists essentially of a a needle electrode element 388 which is of hollow construction having an interior diameter size greater than the exterior diameter size of hypodermic needle 362. The exterior periphery of the hypodermic needle 362 excluding the sharpened ends thereof is provided with a coating of electrical insulating material of a thickness such as to electrically insulate the hollow electrode needle 388 when mounted in surrounding relation to the inner end portion of the hypodermic needle 362 adjacent its connection with the ferrule member 372. The intermediate cylindrical portion 380 of the ferrule member 372 is likewise provided with a coating of electrical insulating material of a thickness to electrically insulate the ferrule member 372 from a second ferrule member 390 disposed in surrounding relation thereto and extending forwardly therefrom in peripheral rigid securement to the rearward exterior periphery of the hollow electrode needle element 362. The electric blood flow stimulating device 316 also includes an annular housing member 392 which is detachably engaged with the forward exterior periphery of the outer tubular member 318 and extends forwardly therefrom in surrounding relation to the reduced forward end portion of the inner tubular member 324 of the injecting device 312. Mounted within the housing member 392 is a battery 394 similar to the battery previously provided, which battery is connected with an electrical circuit 396 similar to the electrical circuit 180 previously described. As before, the electric circuit 396 includes a two lead wire 398 similar to the wire 182, one lead of which is fixed to a contact 400 disposed within the interior periphery of the forward portion of the inner tubular member 324 in a position to be engaged by the exterior periphery of the rearward portion 374 of the ferrule member 372 when the needle 362 has been moved forwardly into penetrating relation with the muscle tissue of the patient. As before, the other lead of the wire 398 is connected with a contact 402 which is positioned within the interior periphery of the forward portion of the inner tubular member 324 in a position to be engaged by the exterior periphery of the ferrule member 390 connected with the hollow electrode needle element 388. Preferably, the exterior periphery of the electrode needle element 388, except for the forward pointed end thereof, is provided with a coating of electrical insulating material similar to the coating on the hypodermic needle 362 as, for example, a suitable shellac or resinous material.

FIG. 5 illustrates the assembled storage position of the apparatus 310 and it will be noted that the stressed spring assembly includes the assembled safety cap 338 which serves to prevent the spring fingers from moving radially inward to release the stressed spring. The cartridge assembly is mounted forwardly within the housing assembly in cooperating relation with the stressed spring assembly. When it is desired to inject the medicaments and apply the blood flow stimulating cycles, the safety cap 338 is initially removed, thus displacing the safety pin 340 from its storage position within the spring fingers and hence permitting the same to move radially inwardly.

The actuation procedure consists in the operator manually gripping the exterior periphery of the outer tubular member 318 and then moving the injector forwardly into contact with the muscle tissue of the patient which is to receive the treatment, as for example, the thigh, calf or upper arm. When the forward end of the inner member 318 is stopped by the patient's thigh, continued forward movement exerted on the exterior periphery of the outer member results in a relative longitudinal movement between rear end walls 350 and 334, causing the frustoconical surface 336 to engage the spring finger surfaces 356 and thus move the same radially inwardly by a camming action so as to disengage the grooves 358 from the catch plate, thus releasing the stressed spring 348. As the stressed spring 348 is released the entire cartridge assembly is moved forwardly within the housing assembly during which time the forward pointed end of the hypodermic needle 362 moves outwardly through the sheath 378 and opening 328 and into the muscle tissue of the patient. Toward the end of this penetrating movement, the sharpened forward end portion of the electrode needle element 388 also penetrates the patient's muscle tissue and contacts 400 and 402 are engaged respectively by ferrule portion 374 and ferrule member 390.

After the cartridge movement has been arrested the liquid medicaments 382 and 385 within the container 360 are placed under added pressure in response to the initial movement of the piston 386 within the container 360, causing the diaphragm 370 sealing the forward end of the liquid medicament 382 to bulge forwardly. In the event that this bulging movement does not serve to burst the diaphragm 370 prior to the engagement with the sharpened rear end 378 of the hypodermic needle 362, the engagement with the sharpened rear end 378 insures that the diaphragm 370 will burst, allowing the pressurized liquid medicament 382 in pressure communication therewith to pass into the forward portion 376 of the ferrule member 372 and forwardly through the hypodermic needle 362 outwardly into the muscle tissue of the patient after which liquid medicament 385 by-passes the periphery of the stopper 384 by the action of by-pass fitment 387 and passes in sequence into the muscle tissue of the patient.

FIG. 6 illustrates the position of the hypodermic needle 362 and electrode needle element 388 when in muscle tissue penetrating position within the patient and it will be noted that the muscle tissue extending between the sharp end of the hypodermic needle 362 add the sharp end of the electrode needle element 388 will connect the electric circuit 396 therethrough so as to apply the repeated blood flow stimulating cycles thereto. The circuit 396 is constructed exactly in accordance with the circuit 180 previously described which is shown in FIG. 4. It will be understood that the embodiment of apparatus 310 is desirable because of its simplicity of construction and economy in manufacture. However it does not provide as stable a mounting as the apparatus 10 over the period of time necessary to achieve the required therapeutic effect by virtue of the injection and the application of the repeated blood flow stimulating cycles.

FIGS. 7 through 12 illustrate another apparatus, generally indicated at 410, embodying the principles of the present invention. As best shown in FIG. 7 the apparatus 410 provides an automatic injecting device 412 and an electric blood flow stimulating device 414 which is separate from the injector device. The apparatus 410 is advantageous in that the blood flow stimulating device 414 can be constructed to provide a zone of stimulation which extends substantially beyond the point of injection in more than one direction. Moreover, the penetrating electrode needle elements can be constructed for stable releasable retention permitting removal of the injected hypodermic needle after the injection has taken place.

It will be understood that the injection device 412 of the apparatus 410 is preferably constructed exactly in accordance with the disclosure contained in U.S. Pat. No. 4,394,863 or the aforesaid concurrently filed application Ser. No. 735,740 filed 5-20-85 in which the plural medicaments are t-PA and hydroxylamin hydrochloride. Consequently, a detailed disclosure of the same herein is not believed to be necessary. It will be understood, however, that the injection device 412 may assume other known configurations.

The blood flow stimulating device 414 includes a two-piece housing assembly consisting of a housing base member 416 and a housing cover member 418 suitably detachably fixed together, as by bolts 420 or the like. Base member 416 provides a lower rearward battery containing compartment 422, an upper rearward compartment 424 and a forward compartment 426.

Mounted for horizontal sliding movement within the upper rearward compartment 424 is a stressed spring assembly 428 releasable to move a needle wire electrode assembly 430 contained within compartment 426 into muscle tissue penetrating relation to a patient. As shown, the stressed spring assembly 428 includes a cross member 432 slidably mounted within compartment 424 and having one end of a pair of coil springs 434 engaged with opposite ends thereof. The opposite end of the pair of coil springs is engaged with a rear wall 436 of the base member 416. Fixed to the central portion of the cross member 432 and extending rearwardly therefrom in parallel relation between the pair of coil springs 434 is an actuating rod 438. Rod 438 extends outwardly through an opening 440 in the rear wall 436 and is formed with a notch 442 in the side thereof intermediate its ends. The configuration of opening 440 and notch 442 is such that the forwardly facing surface defining the notch 442 can be moved into engagement with the rearwardly facing surface of the rear wall 436 defining the area adjacent the opening 440 when the actuating rod 438 is first moved rearwardly a distance to compress springs 434 a predetermined amount and then flexed laterally and released. In order to prevent an undesired disengagement of the notch surface, there is provided a safety pin 444 which is engaged in an opening in a rear bracket or projection 446 on the rear wall 436 in a position to retain the pin 444 in lateral abutting engagement with the laterally flexed activating rod 438 to thereby prevent a lateral flexure of the actuating rod in a direction to disengage the notch surface.

The needle wire electrode assembly 430 includes a pair of laterally spaced parallel tubes 448. Tubes 448 are bent arcuately through a 90° bend and the forward ends thereof are provided with resilient seal plugs 450 which are mounted in suitable openings in the bottom wall of the base member defining the compartment 426. The opposite ends of the guide tubes 448 are fixed within an upright wall 452 of the base member 416 which divides compartment 426 from compartment 424. The rear ends of the tubes are disposed within the forward portion of the compartment 424 and have appropriate annular seals therein for slidably sealingly engaging intermediate exterior peripheral portions of a pair of bendable electrode needle wire elements 454. The ends of the needle elements 454 are disposed within the plugs 450 and the forward portions thereof disposed within the guide tubes 448 are maintained in a sterile condition by virtue of the seal provided by the plugs 450 and the peripheral seal in the opposite ends of the guide tubes.

The rearward ends of the needle wire elements 454 extend within the compartment 424 and are anchored with the forward surface of the cross member 432 when in the cocked position, as shown in FIG. 7. The end of each needle wire element 454 has a lead extending laterally therefrom which terminates in a forwardly facing contact 456. Contacts 456 are adapted to engage rearwardly facing contacts 458 carried by the partition 452. Contacts 458 are suitably electrically connected to a circuit 460 energized by a pair of batteries 462 all of which are disposed within the battery compartment 422. The electric circuit 460 preferably is constructed in the same manner as the circuit 180 previously described and schematically illustrated in FIG. 4. Finally, it will be noted that the housing cover 418 and base member 416 are provided with aligned vertical openings 464.

In the operation of the apparatus 410, the operator first applies the device 414 to the patient adjacent the muscle tissue area where the treatment is to take place. The safety pin 444 is pulled and the actuating rod 438 is moved laterally so as to disengage the surface of the notch 442 from the rear wall surface thus releasing the securement of the stressed springs 434. The spring force of the released springs serves to move the cross member 432 forwardly within the compartment 424 carrying before it the two electrode needle wire elements 454. The forward movement of the wire elements causes the sharpened forward ends thereof to penetrate the resilient seal plugs 450 and to move into the muscle tissue of the patient. The curvature of the guide tubes 448 causes the needle wire elements 454 to move into the muscle tissue of the patient along a curved pattern, as shown in FIG. 12.

The movement of the cross member 432 is stopped by engagement of the electric contacts 456 with the electric contacts 458 which serve to connect the circuit 460 in the manner previously described so as to apply the repetitive blood flow stimulating cycles to the muscle tissue extending between the two penetrated electrode elements 454. The engagement of the electrode elements within the muscle tissue of the patient serves to retain the device 414 in operative position, enabling the operator to grip the separate automatic injector device 412 and to move the same through the openings 464 so that the medicaments thereof will be injected into the muscle tissue between the two electrode elements 454 where the repetitive blood flow stimulating cycles are applied. After the automatic injector device 412 has been operated to discharge the medicaments into the muscle tissue of the patient between the electrode elements, the automatic injector device 412 can be removed, leaving the blood flow stimulating device 414 in operative position applying the repetitive blood flow stimulating cycles until the desired therapeutic effect of reperfusion is secured, if possible.

Referring now more particularly to FIG. 13 there is shown therein still another form of apparatus, generally indicated at 510, which embodies the principles of the present invention. The apparatus 510 as depicted in FIG. 13 includes an automatic injector, generally indicated at 512, of the type disclosed in commonly assigned U.S. patent application Ser. No. 735,995 filed concurrently herewith. The automatic injector 512 which will be described in detail hereinafter, is generally of the type capable of retaining two medicament ingredients separately, one of liquid and the other a dry powder. The operation of the apparatus is such that the liquid medicament ingredient, which may be a diluent, is mixed with the dry medicament ingredient in response to a first predetermined manual actuating procedure. After the operator insures that a mixture of the ingredients has taken place to form a liquid medicament a second manual actuating procedure is performed which has the effect of moving the hypodermic needle into the muscle tissue of the patient and injecting the liquid medicament into the muscle tissue through the hypodermic needle. This apparatus is considered particularly useful in carrying out the present invention in that it has the capability of containing a significant number of different medicaments in a form capable of small volume storage and yet convertible into a liquid form suitable for injection when it is desired to use the apparatus.

The apparatus 510 further includes an electrical stimulating apparatus, generally indicated at 514, for applying to the patient who is to receive the injection repeated blood flow stimulating cycles. The apparatus 514 differs from the apparatus 410 previously described in that the electrodes which are used to apply the electrical stimulus to the patient are external skin engaging electrodes rather than electrode needles which penetrate into the muscle tissue. With the apparatus 514 of FIG. 13 it is possible to achieve the period of electrical stimulus during which the muscle tissue tenses by applying the electrical stimulus to the nerves which effect the tension of the muscle tissue rather than to the muscle tissue itself as is the case with the electrode needle embodiment previously described. Indeed, while muscle tension through nerve electrical stimulus is contemplated so also is direct muscular stimulation through the skin engaging electrodes.

Figure 15:
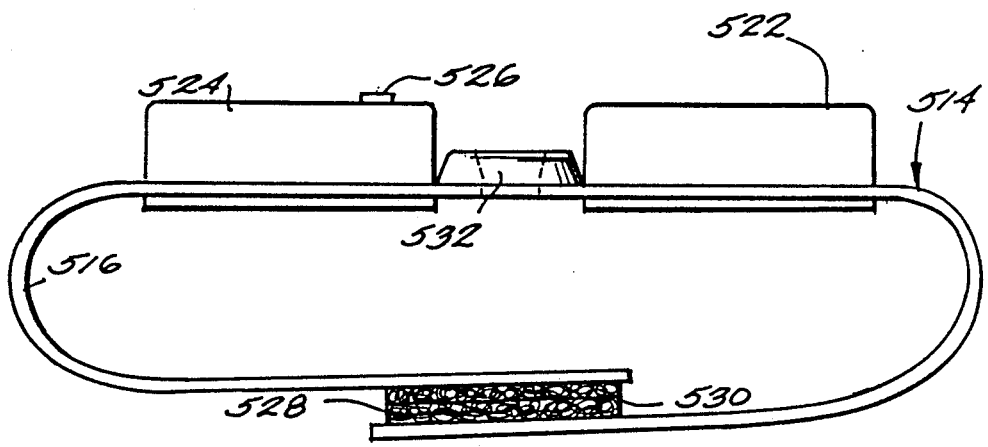
FIG. 15 is a side elevational view of the assembly shown in FIG. 14.
Figure 16:
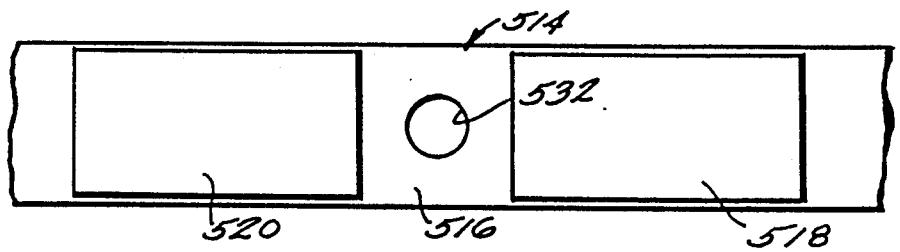
FIG. 16 is a fragmentary bottom plan view of the assembly shown in FIG. 14.

Referring now more particularly to FIGS. 14, 15 and 16, there is shown therein a preferred embodiment of the electrical stimulating apparatus 514. As shown, the apparatus 514 is preferably in the form of an elongated strap 516 which is of generally flexible construction. The strap 516 may be formed of solid plastic or may be of woven material or the like. As best shown in FIGS. 15 and 16, formed on the strap in closely spaced relation on one side thereof there is a pair of electrodes 510 and 520 which may be of any suitable construction. One desirable construction is the provision of a carbon powder loaded vinyl plastic pad. A desirability of this construction is that it may be utilized dry. Nevertheless, it will be understood that conventional wet electrodes may be utilized if desired.

As best shown in FIGS. 14 and 15, fixed to the opposite side of the elongated strap 516 is a pair of housings 522 and 524. Disposed within the housing 522 are batteries similar to the batteries 176 previously described and schematically shown in FIG. 4. Mounted within the opposite housing 524 is circuitry of the type depicted in FIG. 4 except that a manual actuatable switch 526 is provided for controlling whether or not the blood flow stimulating cycles will be applied to the electrodes rather than the engagement of metal hub assemblies 46 and 100 with contact elements 184 and 186.

Mounted on the ends of the strap 516 are Velcro elements 528 and 530. These elements are secured together after the strap has been wrapped around the thigh of the patient, as can be seen in FIG. 13. It will be noted that the strap 516 is provided with target means in the form of a raised opening 532 between the electrode pads 518 and 520 and the housings 522 and 524 for indicating to the operator where the injection should take place to insure that the electrical stimulus will be cooperatively applied.

Referring now more particularly to FIGS. 17 and 18, the apparatus 512 includes an outer housing assembly 612, an inner housing structure 614 mounted within the outer housing assembly for movement forwardly from a storage position into an injecting position. A hypodermic needle assembly 616 is fixed to the forward central portion of the inner housing structure 614 within the outer housing assembly 612 in a sterile condition disposed in a storage position when the inner housing structure 614 is in its storage position and capable of moving outwardly of the outer housing assembly 612 with the inner housing structure 614 for movement into the muscle tissue of a patient when the inner housing structure moves into its injecting position.

Embodied within the inner housing structure 614 is a first medicament container assembly 618 and a side-by-side second medicament container assembly, generally indicated at 620. Operatively associated with the first medicament container assembly 618 and with the inner housing structure 614 is a first stressed spring assembly, generally indicated at 622. A second stressed spring assembly 624 is operatively connected with the second medicament container assembly 620 and with the outer housing assembly 612. As before, a safety cap and releasing assembly, generally indicated at 626, is provided in a storage position for rendering the first and second stressed spring assemblies 622 and 624 incapable of being released. When moved out of its storage position the assembly 626 enables the first stressed spring assembly 622 to be released in response to a first predetermined actuating procedure and then the second stressed spring assembly 624 to be released in response to a second predetermined actuating procedure.

The outer housing assembly 612 is similar to the outer housing assembly 12 previously described in that it includes a main tubular outer housing member 628 having a rear end wall 630 at its rearward end and being open at its forward end. The forward end is closed by a forward housing member 632 which includes a rearwardly extending annular skirt having an interior annular ridge formed therein for engaging within a cooperating annular groove formed in the periphery of the forward end portion of the outer housing member 628. The forward outer housing member 632 also includes a forwardly projecting skin engaging nose portion 634 which is centrally apertured to permit movement of a needle 636 therethrough forming a part of the needle assembly 616.

The inner housing structure 614 includes an inner tubular housing member 638 having an exterior peripheral configuration to slidably engage within the interior peripheral configuration of the outer housing member 628. The inner housing member includes an end wall 640 at its rearward end and, like the outer housing member 628 is open at its forward end. The inner housing structure 614 includes an inner housing member 642 which provides a forward wall having an exterior annular ridge for engaging within an interior peripheral groove formed on the forward end portion of the inner housing member 642. The inner housing member 642 also includes a rearwardly extending portion defining a first container 644 extending rearwardly within the housing member 634 and a second container 646 in side-by-side relation with respect to the first container 644.

It will be noted that the hypodermic needle is of conventional metal configuration having a sharpened forward edge which is engaged within the tip of a resilient sheath 648 so as to close off communication of the hollow interior thereof. The rearward end of the needle communicates with a rearwardly extending passage 650 which is formed in the central forward portion of the inner housing member 642. The rearward end of the passage 650 communicates with the intermediate portion of a cross passage 652, one end of which communicates with the forward end of a passage 654 extending rearwardly in communication with the interior of the first container 644. The first container 644 includes therein a liquid medicament ingredient 656 which is sealingly confined rearwardly by a piston 658 of suitable resilient material so as to be slidably sealingly mounted within the container 644.

The opposite end of the cross passage 652 communicates with a counterbore 660 formed in the forward portion of the member 642. The end of the counterbore 660 is closed by a detachable plug 662. Mounted within the counterbore 660 is a piston valve 664 which, as shown in FIG. 17 is disposed in a storage position closing off communication between the associated end of the cross passage 652 and a short passage 666 extending from the counterbore rearwardly into communication with the second container 646. Mounted within the forward end portion of the second container 646 is a medicament ingredient 668 which preferably is in dry form, specifically a freeze dried powder. The medicament ingredient 668 is sealingly retained within the second container by a piston 670 which is of suitable resilient material like the piston 658 previously described. Mounted in the rearward end portion of the second container 646 in rearwardly spaced relation to the forward piston 670 is a vent piston 672. The vent piston 672 is normally disposed in a storage position spaced inwardly from the rearward end of the second container 646. Formed in the interior periphery of the rearward end portion of the second container 646 is a plurality of annularly spaced vent grooves 674 which extend from the rearward end portion of the piston 672 to the rearward end of the second container 646.

The first stressed spring assembly 622 includes a hollow plunger 676 the forward end of which is flanged, as indicated at 678, and disposed in engagement with the first piston 658 forming a part of the first container 618. The rearward portion of the plunger 676 is slotted, as indicated at 680, to form a plurality of annularly spaced resilient fingers 682 which are integral with the plunger. The fingers 682 are formed with exterior plunger retaining surfaces 684 which face forwardly and outwardly and extend at an angle of approximately 45°. It will be noted that the rearward end wall 640 of the inner housing member 638 is apertured to receive the plunger 676 and is provided with cooperating interior plunger retaining surfaces 686 which face inwardly and rearwardly and extend at an angle of approximately 45°. The fingers 682 of the plunger 676 are also provided with a series of interior plunger releasing surfaces 688. These surfaces are disposed within a common cylindrical plane which has a diameter substantially less than the interior diameter of the hollow piston. The interior plunger releasing surfaces 688 extend from the rearward end of the fingers inwardly a short distance.

Mounted within the interior plunger releasing surfaces 688 of the fingers 682 is a first releasing pin 690 which, as shown, forms a part of the safety cap and releasing assembly 626.

It will be understood that when the releasing pin 690 is disposed in engagement with the interior plunger releasing surfaces 688 the associated fingers 682 are prevented from being deflected radially inwardly. The releasing pin 690 thus serves to insure that the exterior plunger retaining surfaces 684 of the fingers 682 will be maintained in engagement with the cooperating plunger retaining surfaces of the inner housing structure 614. This maintenance is provided notwithstanding the bias which is present by virtue of a stressed coil spring 692 forming a part of the spring assembly 622. Coil spring 692 is mounted over the exterior periphery of the plunger 676 with its forward end in engagement with the flange 678 and its rearward end in engagement with the forwardly facing surface of the rearward end wall 640 of the inner housing structure 614. In order to center the coil spring 692, preferably the end wall 640 is provided with an integral forwardly extending cylindrical skirt portion 694 which surrounds the rearward end portion of the coil spring 692.

The second stressed spring assembly 624 is similar to the first in that it includes a hollow plunger 696 having a flange 698 on the forward exterior periphery thereof and slots 700 formed in the rearward end portion thereof so as to define a series of annularly spaced radially inwardly deflectable spring fingers 702. As before, the spring fingers 702 include exterior plunger retaining surfaces 704 and interior plunger releasing surfaces 706. As shown, the rearward end wall 720 of the outer housing member 628 is apertured to receive the second plunger 696 and includes cooperating rearwardly and inwardly facing plunger retaining surfaces 708. In this regard, it will be noted that the end wall 630 is also apertured to allow free movement of the first plunger 676 therethrough. Similarly, the end wall 640 of the inner housing member 638 is apertured to receive a forwardly extending skirt 709 which surrounds the rearward end portion of a stressed coil spring 710, the forward end of which engages the flange 698 and the rearward end of which engages the forward surface of the end wall 630 of the outer housing member 628 surrounded by the skirt 709.

Mounted within the interior plunger releasing surfaces 706 of the fingers 702 of the second plunger 696 is a second releasing pin, generally indicated at 712. The releasing pin 712 is of the type adapted to release the spring fingers 702 either when moved forwardly or rearwardly with respect to the rear end of the associated spring fingers. As shown, the releasing pin 712 includes a forward movement preventing portion 714 which has a diameter sufficient to engage with the interior plunger releasing surfaces 706 so as to be disposed in engagement therewith when the plunger 696 is in its storage position. The releasing pin 712 also includes an actuating button 716 spaced rearwardly from the movement portion 714 and movable forwardly to move the latter out of its storage position into a releasing position or movable rearwardly to remove the movement preventing portion 714 from its storage position. To enable the forward releasing function to take place, the releasing pin 712 includes a movement enabling portion 718 of reduced diameter fixed between the movement preventing portion 714 and the actuating button 716.

In addition to the releasing pins 690 and 712, the assembly 626 also includes a safety key 720 and a safety cap 722 which is formed as an end wall having a manually engagable annular skirt 724 extending forwardly thereof over a substantial portion of the outer housing member 628. The key 720 is in the form of a rearward wall which is integrally connected with the rear end of the pin 690. The key 720 also includes a cylindrical wall portion 726 extending forwardly from the rear wall and a keyed or dual lug shaped wall portion 728 extending forwardly from the portion 726. Formed in the rear wall of the safety cap 722 is a keyed or dual lug shaped opening 730 of a size to receive the keyed portion 728 therethrough which is rotationally aligned therewith. It will be noted however that when the safety key 720 is turned into the storage position shown so as to be rotationally out of alignment, the keyed portion 728 extends between the cap end wall and the outer housing member end wall so as to prevent forward movement of the cap 722 out of its storage position as shown.

The apparatus 512 is assembled by first assembling the first stressed spring assembly 622 in operative relation with the end wall 640 of the inner housing member 638. This is accomplished by moving the plunger 676 rearwardly within the inner housing member 638 until the rearward end of the plunger fingers 682 engage through the opening defined by the plunger retaining surfaces 686. The releasing pin 690 carried by the safety key 720 is then inserted within the fingers 682 to prevent them from moving radially inwardly. In this way the plunger 676 is prevented from moving forwardly by virtue of the interengagement between the plunger retaining surfaces 684 and 686 thus retaining the coil spring 692 in its stressed condition. Similarly, the second stressed spring assembly 624 is mounted in operative relation with respect to the outer housing member 628 utilizing releasable pin 712. Next, the safety cap 722 is engaged into its storage position with skirt 724 extending over the outer housing member 628 and with the opening 730 receiving the portion 726 of the key 720. Forward movement of the cap is stopped by the engagement of the keyed portion 728 of the safety key 720 between the cap rear wall and the housing member rear wall.

Next, the containers 644 and 646 are separately filled with the respective medicament ingredients 656 and 668 and sealed by the piston valve 666 and plug 662 at their forward ends and with the pistons 658 and 670-672 at their rearward ends. Next, the housing member 642 defining the two containers is mounted within the inner housing member 638 and needle 636 is mounted in place. After the resilient sheath 648 has been mounted over the needle 636, the entire unit containing the two container assemblies 618 and 620, the inner housing structure 614 and needle assembly 616 is moved rearwardly into the outer tubular housing member 628 and the housing member 632 is snapped over the forward end thereof to complete the assembly.

To operate the apparatus 512 the operator first turns the safety key 720 and moves it rearwardly out of its storage position, as shown in FIG. 17. The removal of the safety key 720 carries with it the safety pin 690 and this movement constitutes the first predetermined actuating procedure which effects the release of the first stressed spring assembly 622. In this regard, it will be noted that the angle of the plunger movement preventing surfaces 684 and 686 are such that as soon as the releasing pin 690 is removed from its storage position, the stress of spring 692 will effect sufficient forward movement of the plunger 676 to cause the spring fingers 682 to be moved radially inwardly until the surface 684 disengages from the surface 686 and then the stressed spring 692 is capable of advancing the plunger 676 forwardly through an operative stroke.

Since the forward flanged end 678 of the plunger 676 is in engagement with piston 658 which in turn is in engagement with the liquid medicament ingredient 656, the force of the released stressed spring 692 serves to increase the pressure within the liquid medicament ingredient 656. This pressure is transmitted to the inner housing member 642 and the liquid within the passage 654 and cross passage 652 therein. The force required to effect movement of the piston valve 664 is considerably less than the force required to effect movement of the entire inner housing member 620 and consequently the piston valve 664 will be moved into a position uncovering the passage 666 so as to allow the pressurized liquid medicament ingredient 656 to pass into the second container 646 to mix with the medicament ingredient 668 therein. As the liquid medicament ingredient 656 flows into the second container 646 piston 670 will be moved rearwardly. This movement in turn causes the air rearwardly of the piston to increase and this increase in pressure in turn builds up until it is sufficient to effect a rearward movement of the vent piston 672. The vent piston 672 moves rearwardly until it engages the forward flanged end 698 of the plunger 696. In this position vent grooves 674 are communicated with the space within the second container 646 forwardly of the vent piston 672 thus exhausting the pressure to atmosphere and allowing the piston 670 to move freely rearwardly in response to the flow of liquid medicament ingredient 656 from the first container into the second container. When this movement has been completed by virtue of the movement of the piston 658 into its forwardmost position, the operator may at that time shake the apparatus to insure that the liquid medicament 656 will be mixed thoroughly with the medicament ingredient 668 within the second container.

Next, the operator performs the second predetermined manual actuating procedure which has the effect of injecting the liquid medicament formed during the mixing operation. The actuating procedure includes grasping the skirt 724 of the safety cap 722 and moving the nose portion 664 of the outer housing assembly 612 into engagement with the skin of the patient in the area which is to receive the injection, as for example, the thigh. Continued forward movement on the skirt 724 has the effect of effecting the forward movement of the latter with respect to the outer housing assembly 612 during which movement the rear wall of the safety cap 626 will engage the actuating button 712 and move the same forwardly until movement preventing portion 714 thereof is disengaged from the movement preventing surfaces 706 of the spring fingers. Immediately thereafter the force of spring 710 and the inclination of the surfaces 704 and 708 are such as to cause the plunger 696 to move forwardly deforming the spring fingers 702 radially inwardly until surfaces 704 are disengaged from the surfaces 708. Continued forward movement of the plunger 698 acts through vent piston 672, piston 670 and the liquid medicament forwardly thereof to move the inner housing structure 620 forwardly. During the initial forward movement of the inner housing structure 620, needle 636 pierces through the end of the resilient sheath 648 and extends outwardly beyond the housing nose portion 634 into the muscle tissue of the patient. This outward movement is arrested by the compression of the resilient sheath 648 against the housing portion 634. As soon as the forward movement of the inner housing structure 620 is arrested, continued forward movement of the plunger 696 will result in an outward movement of the liquid medicament forward of the plunger 670 outwardly of the second container through passage 666, cross passage 652, passage 650 and into the hypodermic needle 636 and finally outwardly into the muscle tissue of the patient. This movement of the liquid ingredient from the container 646 into the muscle tissue of the patient continues until the piston 670 reaches its forwardmost position within the container. As soon as this injection procedure has been accomplished, the operator simply removes the device from the patient and in this fashion withdraws the needle from the muscle tissue.

The apparatus 510 shown being used in FIG. 13 is a preferred apparatus particularly in administering t-PA in accordance with the system disclosed in my copending application Ser. No. 638,695. Advantages of the apparatus 510 as compared with those previously disclosed include the following. First, with respect to the embodiments of FIGS. 1-4, injecting the apparatus 512 of the apparatus 510 requires only a single needle to inject more medicament than is the case with injector 10. The electrical stimulating apparatus 514 of the apparatus 510 eliminates the need to retain needles in the patients muscle tissue for an extended period and the need for handling during that time a protruding housing. Moreover, the battery and circuitry of apparatus 514 can be reused and need not be discarded with the injecting device 512 as is the case with apparatus 10.

The same advantages prevail with respect to the apparatus 310 of FIGS. 5 and 6 except that this embodiment may be regarded as having the equivalent of a single needle but, of course, its medicament capacity is likewise diminished. The apparatus 410 of FIGS. 7-12 includes a reusable electrical stimulating apparatus 414, however, the exterior electrode pads of the apparatus 510 may be more patient friendly than the needle electrodes of the apparatus 414. Moreover, apparatus 512 presents a highly advantageous ability to deliver a maximum amount of medicament.

With respect to the medicament capacity advantages of the automatic injecting apparatus 512, it is contemplated that the dry medicament ingredient 668 could include any one or any combination of or preferably all of the following medicament ingredients in a dry form, preferably a freeze dried powder. (1) a clot selective coronary thrombolytic agent, such as t-PA; (2) a blood absorption enhancing agent, such as hydroxylamine hydrochloride; (3) an anti-arrythmic agent, such as lidocaine; (4) an anti-reclotting agent, either of the thromboxane synthetase inhibitor type, such as dazoxiben, or of the antagonist for the receptor of thromboxane A, such as SQ 27,427; and (5) a reperfusion damage preventing agent, such as superoxide dismutase of S-aminotrimethyleneaminoethyl thiophosphate.

It will be understood that where combinations of these ingredients are utilized, the ingredients may be separated by dissolvable independent container bags or divider disks. The liquid medicament ingredient 656 is preferably a diluent, such as sterile water. The specific dosages of the medicament ingredients described above can be obtained by reference to commonly assigned patent applications Ser. Nos. 38,695 filed Aug. 8 1984, 708,845 filed Mar. 6, 1985, and Ser. No. 735,734 filed concurrently herewith.

It will be understood that in using the apparatus 510, the apparatus 514 is first strapped on the patient into position shown in FIG. 13. Next, the automatic injecting apparatus 512 is, actuated as previously indicated, with the final injection function taking place at the target area through the opening 532. After injection has been completed, apparatus 512 is withdrawn and switch 526 is turned on for a period sufficient to achieve the desired therapeutic effect, if possible. Since the circuitry of the apparatus 514 is the same as the circuitry 180 previously described its operation will be apparent.

The automatic injecting apparatus 412, shown in FIG. 7, since it is a single dosage unit is particularly suitable for use in treating a soman induced convulsive patient in which case it contains an anticonvulsive liquid benzodiazepine medicament, such as Midazolam. This injector 412 is also useful with the apparatus 514 in lieu of apparatus 414.

It will also be understood that while the use of apparatus 510 is particularly desirable where as many as five medicaments are to be injected as aforesaid, it is within the contemplation of the present invention to operate five successive single dosage units 412 containing the five different medicaments and to thereafter operate the apparatus 514. Moreover, the apparatus 10 minus the stimulating mechanism 16 presents a desirable unit to use with the apparatus 514 when only the three medicaments 52, 56 and 98 are to be injected. Likewise, the injecting apparatus 310 minus the electrical stimulating mechanism 314 could be used with the apparatus 514 when only two medicaments 382 and 385 are to be injected. A combination of the modified units 10 and 310 could be used to inject all five agents or each could be used in combination with one or more single units 410.

For purposes of background and elaboration of the present disclosure, the disclosures of the patent applications, patents and publications herein mentioned are incorporated by reference into the present specification.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. A method of treating a patient with liquid medicament under circumstances where intravenous injection is not practical but the fast response time of an intravenous injection is desirable, said method comprising the steps of
    injecting liquid medicament into the muscle tissue of the patient,
    applying to the patient who has received the injection repeated blood flow stimulating cycles, each of which includes a period of electrical stimulus during which the muscle tissue which received the liquid medicament tenses followed by a period of no electrical stimulus during which the muscle tissue which received the liquid medicament is allowed to relax inducing enhanced blood flow within the muscle tissue, and
    continuing the application of the repeated blood flow stimulating cycles until the injected liquid medicament has been sufficiently absorbed into the blood to achieve a desired possible patient response.

2. A method as defined in claim 1 wherein the treatment is of a soman induced convulsive patient under emergency conditions with an anti-convulsive liquid benzodiazepine medicament.

3. A method as defined in claim 2 wherein the liquid benzodiazepine medicament is Midazolam.

4. A method as defined in claim 1 wherein the treatment is a reperfusion treatment of a patient undergoing heart attack symptoms with a liquid medicament having a clot-selective coronary thrombolytic agent therein.

5. A method as defined in claim 4 wherein said coronary thrombolytic agent is t-PA.

6. A method as defined in claim 5 wherein said liquid medicament includes a blood absorption enhancing agent.

7. A method as defined in claim 6 wherein said blood absorption enhancing agent is hydroxylamine hydrochloride.

8. A method as defined in claim 7 wherein said liquid medicament includes an anti-arrythmic agent.

9. A method as defined in claim 8 wherein said anti-arrythmic agent is lidocaine.

10. A method as defined in claim 9 wherein said liquid medicament includes an anti-reclotting agent.

11. A method as defined in claim 10 wherein said anti-reclotting agent is a thromboxane synthetase inhibitor.

12. A method as defined in claim 11 wherein said thromboxane synthetase inhibitor is dazoxiben.

13. A method as defined in claim 10 wherein said anti-reclotting agent is an antagonist for the receptor of thromboxane A.

14. A method as defined in claim 13 wherein said antagonist for the receptor of thromboxane A is SQ 27,427.

15. A method as defined in claim 10 wherein said liquid medicament includes a reperfusion damage preventing agent.

16. A method as defined in claim 15 wherein said reperfusion damage preventing agent is superoxide dismutase.

17. A method as defined in claim 15 wherein said reperfusion damage preventing agent is S-aminotrimethyleneaminoethyl thiophosphate.

18. A method as defined in claim 4 wherein said liquid medicament includes a blood absorption enhancing agent.

19. A method as defined in claim 18 wherein said blood absorption enhancing agent is hydroxylamine hydrochloride.

20. A method as defined in claim 18 wherein said liquid medicament includes an anti-arrythmic agent.

21. A method as defined in claim 20 wherein said anti-arrythmic agent is lidocaine.

22. A method as defined in claim 18 wherein said liquid medicament includes an anti-reclotting agent.

23. A method as defined in claim 22 wherein said anti-reclotting agent is a thromboxane synthetase inhibitor.

24. A method as defined in claim 23 wherein said thromboxane synthetase inhibitor is dazoxiben.

25. A method as defined in claim 22 wherein said anti-reclotting agent is an antagonist for the receptor of thromboxane A.

26. A method as defined in claim 25 wherein said antagonist for the receptor of thromboxane A is SQ 27,427.

27. A method as defined in claim 18 wherein said liquid medicament includes a reperfusion damage preventing agent.

28. A method as defined in claim 27 wherein said reperfusion damage preventing agent is superoxide dismutase.

29. A method as defined in claim 27 wherein said reperfusion damage preventing agent is S-aminotrimethyleneaminoethyl thiophosphate.

30. A method as defined in claim 4 wherein said liquid medicament includes an anti-reclotting agent.

31. A method as defined in claim 30 wherein said anti-reclotting agent is a thromboxane synthetase inhibitor.

32. A method as defined in claim 31 wherein said thromboxane synthetase inhibitor is dazoxiben.

33. A method as defined in claim 30 wherein said anti-reclotting agent is an antagonist for the receptor of thromboxane A.

34. A method as defined in claim 33 wherein said antagonist for the receptor of thromboxane A is SQ 27,427.

35. A method as defined in claim 4 wherein said liquid medicament includes a reperfusion damage preventing agent.

36. A method as defined in claim 35 wherein said reperfusion damage preventing agent is superoxide dismutase.

37. A method as defined in claim 35 wherein said reperfusion damage preventing agent is S-aminotrimethyleneaminoethyl thiophosphate.

* * * * *